(12) United States Patent
Gaudernack et al.

(10) Patent No.: US 12,168,045 B2
(45) Date of Patent: *Dec. 17, 2024

(54) VACCINE IN COMBINATION WITH AN IMMUNE CHECKPOINT INHIBITOR FOR USE IN TREATING CANCER

(71) Applicant: Ultimovacs AS, Oslo (NO)

(72) Inventors: Gustav Gaudernack, Sandvika (NO); Audun Tornes, Drammen (NO)

(73) Assignee: Ultimovacs ASA, Oslo (NO)

( * ) Notice: Subject to any disclaimer, the term of this patent is extended or adjusted under 35 U.S.C. 154(b) by 0 days.

This patent is subject to a terminal disclaimer.

(21) Appl. No.: 17/818,584

(22) Filed: Aug. 9, 2022

(65) Prior Publication Data

US 2023/0049012 A1 Feb. 16, 2023

Related U.S. Application Data

(63) Continuation of application No. 16/306,352, filed as application No. PCT/EP2017/063589 on Jun. 2, 2017, now Pat. No. 11,419,927.

(30) Foreign Application Priority Data

Jun. 2, 2016 (EP) ..................... 16172760

(51) Int. Cl.
| | |
|---|---|
| *A61K 39/395* | (2006.01) |
| *A61K 39/00* | (2006.01) |
| *A61P 35/00* | (2006.01) |
| *A61P 35/04* | (2006.01) |
| *C07K 16/28* | (2006.01) |

(52) U.S. Cl.
CPC .. *A61K 39/001157* (2018.08); *A61K 39/0011* (2013.01); *A61K 39/00115* (2018.08); *A61K 39/001154* (2018.08); *A61K 39/39558* (2013.01); *A61P 35/00* (2018.01); *A61P 35/04* (2018.01); *C07K 16/2818* (2013.01); *A61K 2039/505* (2013.01); *A61K 2039/53* (2013.01); *A61K 2039/70* (2013.01); *C07K 2317/21* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 7,488,802 B2 | 2/2009 | Collins et al. | |
| 7,635,757 B2 | 12/2009 | Freeman et al. | |
| 7,943,743 B2 | 5/2011 | Korman et al. | |
| 8,008,449 B2 | 8/2011 | Korman et al. | |
| 8,168,757 B2 | 5/2012 | Finnefrock et al. | |
| 8,217,149 B2 | 7/2012 | Irving et al. | |
| 2009/0317368 A1 | 12/2009 | Chen | |
| 2013/0071428 A1 | 3/2013 | Ossendorp et al. | |
| 2015/0224182 A1 | 8/2015 | Hunt et al. | |
| 2016/0030536 A1 | 2/2016 | Weiner et al. | |
| 2016/0058852 A1 | 3/2016 | Ter Meulen et al. | |
| 2016/0106830 A1 | 4/2016 | Georges et al. | |
| 2016/0130345 A1 | 5/2016 | Fotin-Mleczek et al. | |
| 2017/0202938 A1 | 7/2017 | Binder et al. | |
| 2018/0037654 A1 | 2/2018 | Van Eenennaam et al. | |

FOREIGN PATENT DOCUMENTS

| | | |
|---|---|---|
| WO | WO03086459 | 10/2003 |
| WO | WO2007113648 | 10/2007 |
| WO | WO 2011/101173 A1 | 8/2011 |
| WO | WO2011101173 | 8/2011 |
| WO | WO 2011/0115483 | 9/2011 |
| WO | WO2012037551 | 3/2012 |
| WO | WO2014127917 | 8/2014 |
| WO | WO2015033140 | 3/2015 |
| WO | WO2015037000 | 3/2015 |
| WO | WO2015089114 | 6/2015 |
| WO | WO2015095811 | 6/2015 |
| WO | WO2015128313 | 9/2015 |
| WO | WO2015175334 | 11/2015 |
| WO | WO2015175340 | 11/2015 |
| WO | WO2016004213 | 1/2016 |
| WO | WO2016007499 | 1/2016 |
| WO | WO2016007504 | 1/2016 |
| WO | WO2016011362 | 1/2016 |
| WO | WO2016011386 | 1/2016 |
| WO | WO2016025647 | 2/2016 |
| WO | WO2016063263 | 4/2016 |
| WO | WO2016073759 | 5/2016 |
| WO | WO 2017/207814 | 12/2017 |

OTHER PUBLICATIONS

Park, J.-J., et al., "Checkpoint Inhibition Through Small Molecule-Induced Internalization of Programmed Death-Ligand 1," Nature Communication, 12(1):1-11 (2021).
Aamdal, E., et al., "Combining the telomerase peptide cancer vaccine UV1 with CTLA-4 blockade in patients with metastatic malignant melanoma: Proof of principle and early clinical reports from a phase I/IIa trial," Oslo University Hospital, 1-2 (2015).
Aamdal, E., et al., "Combining the telomerase peptide cancer vaccine UV1 with CTLA-4 blockade in patients with metastatic malignant melanoma—proof of principle and early clinical reports from a phase I/IIa trial," Oslo University Hospital. Poster. (2015).
Ahmadzadeh, M., et al., "Tumor Antigen-Specific CD8 T Cells Infiltrating the Tumor Express High Levels of PD-1 and Are Functionally Impaired," Blood, 114(8): 1537-1544 (2009).

(Continued)

*Primary Examiner* — Michael D Pak
(74) *Attorney, Agent, or Firm* — HoustonHogle LLP

(57) ABSTRACT

A polypeptide for use in medicine is provided. The polypeptide is administered simultaneously, separately or sequentially with an immune checkpoint inhibitor. The polypeptide comprises at least one polypeptide comprising a region of at least 12 amino acids of a self-antigen or a sequence having at least 80% identity to the region. The polypeptide is less than 100 amino acids in length.

32 Claims, 8 Drawing Sheets

Specification includes a Sequence Listing.

(56) References Cited

OTHER PUBLICATIONS

Altschul, S. F., et al., "Gapped BLAST and PSI-BLAST: a new generation of protein database search programs," Nucleic Acids Res., 25(17):3389-3402 (1997).
Andre, F., et al,, "Molecular Pathways: Involvement of Immune Pathways in the Therapeutic Response and Outcome in Breast Cancer," Clin. Cancer Res., 19(1): 28-33 (2013).
Anonymous, "NCI Dictionary of Cancer Terms, " National Cancer Institute, 1-2 (2018).
Aqui, N.A., et al., "Survivin as a Universal Tumor Antigen for Novel Cancer Immunotherapy," Cancer Biology & Theraphy, 7(12): 1888-1889 (2008).
Bearss, D.J., et al., "Telomere Maintenance Mechanisms as a Target for Drug Development, " Oncogene, 19(56): 6632-6641 (2000).
Brunsvig, P.F., et al., "Telomerase Peptide Vaccination: A Phase I/II Study in Patients with Non-Small Cell Lung Cancer," Cancer Immunol. Immunother., 55(12):1553-1564 (2006).
Buchbinder, E.I., et al., "CTLA-4 and PD-1 Pathways," American Journal of Clinical Oncology, 39(1): 98-106 (2016).
Butte, M.J., et al., "Programmed Death-1 Ligand 1 Interacts Specifically with the B7-1 Costimulatory Molecule to Inhibit T Cell Responses," Immunity, 27: 111-122 (2007).
Dengjel, J., et al., "Unexpected Abundance of HLA Class II Presented Peptides in Primary Renal Cell Carcinomas," Clin. Cancer Res, 12(14): 4163-4170 (2006).
Dong, H., et al., "Tumor-Associated B7-H1 Promotes T-Cell Apoptosis: A Potential Mechanism of Immune Evasion," Nat. Med. 8(8): 793-800 (2002).
Dong, H., et al., "B7-H1, a Third Member of the B7 Family, Co-Stimulates T-Cell Proliferation and Interleukin-10 Secretion," Nat. Med., 5(12): 1365-1369 (1999).
Doonan, B.P., et al., "Prostate Cancer Immunotherapy: Exploiting the HLA Class II Pathway in Vaccine Design," J. Clin Cell Immunol., 6(4): 1-16 (2015).
Foy, S.P., et al., "Poxvirus-Based Active Immunotherapy Synergizes with CTLA-4 Blockade to Increase Survival in a Murine Tumor Model by Improving the Magniture and Quality of Cytotoxic T Cells," Cancer Immunol. Immunother., 65(5):537-549 (2016).
Fransen, M.F., et al., "Controlled Local Delivery of CTLA-4 Blocking Antibody Induces CD8+ T-Cell-Dependent Tumor Eradication and Decreases Risk of Toxic Side Effects," Clin. Cancer Res. 19(19): 5381-5389 (2013).
Fransen, M.F., et al., "Local Immunomodulation for Cancer Therapy: Providing Treatment Where Needed," Oncoimmunology, 2(11): e26493 (2013).
Freeman, G.J., et al., "Engagement of the PD-1 Immunoinhibitory Receptor by a Novel B7 Family Member Leads to Negative Regulation of Lymphocyte Activation," J. Exp. Med., 192 (7): 1027-1034 (2000).
Gerber, H.-P., et al., "Combining Antibody-Drug Conjugates and Immune-Mediated Cancer Therapy: What to expect?," Biochemical Pharmacology, 102: 1-6 (2016).
Gjertsen, M.K., et al., "HLA-A3 restricted mutant ras specific cytotoxic T-lymphocytes induced by vaccination with T-helper epitopes," J. Mol. Med. (Berl), 81(1): 43-50 (2003).
Gribben, J.G., et al., "Unexpected association between induction of immunity to the universal tumor antigen CYP1B1 and response to next therapy," Clin. Cancer Res., 11 (12):4430-4436 (2005).
Herbst, R.S., et al., "A Study of MPDL3280A, An Engineered PD-L1 Antibody in Patients with Locally Advanced or Matastic Tumors," Annu. Meet Am. Soc. Clin. Oncol., Chicago, May 31-Jun. 4. 2013.
Hodi, F.S., et al., "Improved survival with ipilimumab in patients with metastatic melanoma," N. Engl. J. Med., 363(8): 711-723 (2010).
Hui, E., et al., "T Cell Costimulatory Receptor CD28 is a Primary Target for PD-1-Mediated Inhibition," Science, 355: 1428-1433 (2017).
Inderberg, E.M., et al., "UV1—a second-generation, peptide-based, therapeutic cancer vaccine (TCV) targeting the Reverse Transcriptase subunit of human Telomerase (hTERT)," Oslo University Hospital, 1 (2016).
Inderberg, E.M., et al., "UV1—a second-generation, peptide-based, therapeutic cancer vaccine targeting the Reverse Transcriptase subunit of human Telomerase (hTERT)," Oslo University Hospital, 1 (2016).
Inderberg, E.M., et al., "UV1-A Second Generation, Peptide Based Therapeutic Cancer Vaccine Targeting the Reverse Transcriptase Subunit of Human Telomerase (hTERT)," Poster. (2016).
International Preliminary Report on Patentability, mailed on Sep. 19, 2018, from International Application No. PCT/EP2017/063589, filed on Jun. 2, 2017. 10 pages.
International Search Report, mailed on Sep. 11, 2017, from International Application No. PCT/EP2017/063589, filed on Jun. 2, 2017. 7 pages.
Kenter, G.G., et al., "Vaccination Against HPV-16 Oncoproteins for Vulvar Intraepithelial Neoplasia," N. Engl. J. Med., 361(19): 1838-1847 (2009).
Kim, N.W., et al., "Specific association of human telomerase activity with immortal cells and cancer," Science, 266(5193): 2011-2015 (1994).
Kirkwood, J.M., et al., "Phase II trial of tremelimumab (CP-675,206) in patients with advanced refractory or relapsed melanoma," Clin. Cancer Res., 16(3): 1042-1048 (2010).
Kirner, A., et al., "IMA901: A Multi-Peptide Cancer Vaccine for Treatment of Renal Cell Cancer," Human Vaccines & Immunotherapeutics, 10(11): 3179-3189 (2014).
Kyi, C., et al., "Checkpoint blocking antibodies in cancer immunotherapy," FEBS Lett., 588 (2): 368-376 (2013).
Kyte, J.A., et al., "Telomerase peptide vaccination combined with temozolomide: a clinical trial in stage IV melanoma patients," Clin. Cancer Res., 7(13): 4568-4580 (2011).
Latchman, Y., et al., "PD-L2 is a second ligand for PD-1 and inhibits T cell activation," Nat. Immunol. 2(3): 261-268 (2001).
Lee, L., et al., "Immune Checkpoint Inhibitors: An Introduction to the Next-Generation Cancer Immunotherapy," Journal of Clinical Pharmacology, 56(2): 157-169 (2015).
Manlove, L.S., "Anti-Leukemia Immunity is Enabled by Unmasking Cross-Reactive Antigens with Vaccination and Checkpoint Blockade," University of Minnesota, i-206 (2015).
Manlove, L.S., et al., "Heterologous Vaccination and Checkpoint Blockade Synergize to Induce Anti-Leukemia Immunity," J. Immunol., 196(11): 4793-4804 (2016).
May, K.F., et al., "Prostate cancer immunotherapy," Clin. Cancer Res., 17(16): 5233-5238 (2011).
McDermott, D., et al., "Efficacy and safety of ipilimumab in metastatic melanoma patients surviving more than 2 years following treatment in a phase III trial (MDX010-20)," Ann. Oncol., 24(10): 2694-2698 (2013).
Melero, I., et al., "Therapeutic vaccines for cancer: an overview of clinical trials," Nat. Rev. Clin. Oncol., 11(9): 509-524 (2014).
Met, O., et al., "The effect of a therapeutic dendritic cell-based cancer vaccination depends on the blockage of CTLA-4 signaling," Cancer Lett., 231(2): 247-256 (2006).
O'Donnell, J.S., et al., "PD1 Functions by Inhibiting CD28-Mediated Co-Stimualtion," Clinical & Translational Immunology, 6(e138): 1-3 (2017).
Okazaki, T., et al., "PD-1 and PD-1 ligands: from discovery to clinical application," Intern. Immun., 19(7): 813-824 (2007).
Page, D.B., et al., "Immune Modulations in Cancer with Antibodies," Annual Review of Medicine, 65:185-202 (2014).
Park, J.-S., et al., "Topoisomerase II alpha as a universal tumor antigen: antitumor immunity in murine tumor models and H-2K(b)-restricted T cell epitope," Cancer Immunol Immunother., 59(5):747-757 (2010).
Park, J.J., et al., "B7-H1/CD80 interaction is required for the induction and maintenance of peripheral T-cell tolerance," Blood, 116(8): 1291-1298 (2010).
Petrovsky, N., "Vaccine adjuvants: current state and future trends," Immunol. Cell Biol., 82 (5): 488-496 (2004).
Postow, M.A., et al., "Immune Checkpoint Blockade in Cancer Therapy," J. Clin. Oncol., 33 (17): 1974-1982 (2015).

(56) References Cited

OTHER PUBLICATIONS

Ribas, A., et al., "Phase III randomized clinical trial comparing tremelimumab with standard-of-care chemotherapy in patients with advanced melanoma," J. Clin. Oncol., 31 (5): 616-622 (2013).
Robert, C., et al., "Ipilimumab plus dacarbazine for previously untreated metastatic melanoma," N. Engl. J. Med., 364 (26): 2517-2526 (2011).
Robert, C., et al., "Nivolumab in Previously Untreated Melanoma without BRAF Mutation," NEJM, 372(4): 320-330 (2014).
Robert, C., et al., "Pembrolizumab Versus Ipilimumab in Advanced Melanoma," NEJM, 372 (26):2521-2532 (2015).
Robert, C., et al., "Rembrolizumab Versus Ipilimumab in Advanced Melanoma (Keynote-006): Post-Hoc 5-Year Results from an Open-Label, Multicentre, Randomised, Controlled, Phase 3 Study," Lancel Oncol., 20: 1239-1251 (2019).
Sarnaik, A.A., et al., "Extended dose ipilimumab with a peptide vaccine: immune correlates associated with clinical benefit in patients with resected high-risk stage IIIc/IV melanoma," Clin. Cancer Res., 17(4): 896-906 (2011).
Schachter, J., et al., "Pembrolizumab Versus Ipilimumab for Advanced Melanoma: Final Overall Survival Anaysis of Keynote-006," Journal of Clinical Oncology, 34(15) Suppl: 9504. 5 pages. (2016).
Schachter, J., et al., "Pembrolizumab Versus Ipilimumab for Advanced Melanoma: Final Overall Survival Results of a Multicentre, Randomised, Open-Label Phase 3 Study (Keynote-006)," Lancet: 390: 1853-1862 (2017).
Sharon, E., et al., "Immune Checkpoints in Cancer Clinical Trials," Chin J Cancer, 33(9): 434-444 (2014).
Shay, J.W., et al., "Telomeres and telomerase in normal and cancer stem cells, " FEBS Lett., 584(17): 3819-3825 (2010).
Shimodaira, S., et al., "Dendritic Cell-Based Adjuvant Vaccination Targeting Wilms' Tumor 1 in Patients with Advanced Colorectal Cancer," Vaccines, 3: 1004-1018 (2015).
Sorensen, R.B., et al., "A survivin specific T-cell clone from a breast cancer patient display universal tumor cell lysis," Cancer Biol. Ther., 7(12):1885-1887 (2008).
Thompson, R.H., et al., "Tumor B7-H1 is associated with poor prognosis in renal cell carcinoma patients with long-term follow-up," Cancer Res., 66(7): 3381-3385 (2006).
Topalian et al., Presented at Annu. Meet. Am. Soc. Clin. Oncol., Chicago, May 31-Jun. 4. 2013).
Topalian, S.L., et al., "Safety, activity, and immune correlates of anti-PD-1 antibody in cancer," N. Engl. J. Med., 366 (26): 2443-2454 (2012).
Tseng, S.Y., et al., "B7-DC, a new dendritic cell molecule with potent costimulatory properties for T cells," J. Exp. Med., 193(7): 839-846 (2001).
Van Poelgeest, M.I.E., et al., "Vaccination Against Oncoproteins of HPV16 for Noninvasive Vulvar/Vaginal Lesions: Lesion Clearance is Related to the Strength of the T-Cell Response," Clin Cancer Res, 22(10): 2342-2350 (2016).
Walker, L.S.K., "PD-1 and CTLA4: Two Checkpoints, One Pathway?" Sci Immunol., 2(11): 1-5 (2017).
Welters, M.J., et al., "Vaccination During Myeloid Cell Depletion by Cancer Chemotherapy Fosters Robust T Cell Responses," www. ScienceTranslationMedicine.org, 8(334): 1-12 (2016).
Welters, M.J.P., et al., "Induction of Tumor-Specific CD4+ and CD8+ T-Cell Immunity in Cervical Cancer Patients by a Human Papillomavirus Type 16 E6 and E7 Long Peptides Vaccine," Clin Cancer Res, 14(1): 178-187 (2008).
Williams, E.L., et al., "Immunomodulatory monoclonal antibodies combined with peptide vaccination provide potent immunotherapy in an aggressive murine neuroblastoma model.," Clin. Cancer Res. 19(13) 3545-3555 (2013).
Wobser, M., et al., "Complete remission of liver metastasis of pancreatic cancer under vaccination with a HLA-A2 restricted peptide derived from the universal tumor antigen survivin," Cancer Immunol. Immunother. 55(10): 1294-1298 (2006).
Wolchok, J.D., et al., "Safety and Clinical Activity of Nivolumab (Anti-PD-1, BMS-936558, ONO-4538) in Combination with Ipilimumab in Patients (pts) with Advanced Melanoma (MEL)," J Clin Oncol, 31, 2013 (suppl 9012): 1-2 (2013).
Written Opinion, mailed on Sep. 11, 2017, from International Application No. PCT/EP2017/063589, filed on Jun. 2, 2017. 12 pages.
Yuan, J., et al., "CTLA-4 blockade increases antigen-specific CD8(+) T cells in prevaccinated patients with melanoma: three cases," Cancer Immunol. Immunother., 60(8): 1137-1146 (2011).
Zanetti, M., "A second chance for telomerase reverse transcriptase in anticancer immunotherapy," Nat. Rev. Clin. Oncol., 14(2): 115-128 (2016).
Zhou, J., et al., "Immunity to the Vacuolar ATPase Complex Accesory Unit ATP6S1 in Patients with Malignant Melanoma," Cancer Immunol Res: 3(1): 59-67 (2015).
Written Opinion of the International Preliminary Examining Authority, mailed on Jun. 25, 2018, from International Application No. PCT/EP2017/063589, filed on Jun. 2, 2017. 9 pages.
EudraCT No. 2012-001852-20: https://clinicaltrials.gov/ct2/show/NCT01789099, 8 pages.
EudraCT No. 2012-002411-26: https://clinicaltrials.gov/ct2/show/NCT01784913, 8 pages.
EudraCT No. 2013-005582-39: https://clinicaltrials.gov/ct2/show/NCT02275416, 7 pages.
"Phase III Open Label First Line Therapy Study of MEDI 4736 (Durvalumab) With or Without Tremelimumab Versus SOC in Non Small-Cell Lung Cancer (NSCLC). (MYSTIC)", Phase_III_AstraZeneca_full, 2015, pp. 11.
"Atezolizumab (MPDL3280A, RO5541267, Tecentriq®)" National Cancer Institute, 2017, pp. 2.
"Phase III Open Label First Line Therapy Study of MEDI 4736 (Durvalumab) With or Without Tremelimumab Versus SOC in Non Small-Cell Lung Cancer (NSCLC). (MYSTIC)" AstraZeneca, 2015, pp. 3.
"Multiple Ascending Dose (MDX1105-01) (Anti-PDL1)" Bristol-Myers Squibb, 2008, pp. 4.
International Preliminary Report on Patentability mailed on Oct. 13, 2023, from International Application No. PCT/EP2022/065777, filed on Jun. 9, 2022. 17 pages.
Zhang, L., et al., "TEPITOPEpan: extending TEPITOPE for peptide binding prediction covering over 700 HLA-DR molecules," PLoS One, 7(2): e30483: 1-10 (2012).
Written Opinion of the International Searching Authority, mailed on Dec. 7, 2022, from International Application No. PCT/EP2022/065777, filed on Jun. 9, 2022. 11 pages.
Stern, L.J., et al., "The melting pot of the MHC II peptidome," Curr Opin Immunol., 40:70-77 (2016).
Rosalia, R.A., et al., "Dendritic cells process synthetic long peptides better than whole protein, improving antigen presentation and T-cell activation," Eur J Immunol., 43(10): 2554-2565 (2013).
Rice, P., et al., "EMBOSS: the European Molecular Biology Open Software Suite," Trends Genet., 16(6): 276-277 (2000).
Muntasell, A., et al., "HLA-DR4 molecules in neuroendocrine epithelial cells associate to a heterogeneous repertoire of cytoplasmic and surface self peptides," J. Immunol.; 169(9).
Mangsbo, S.M., et al.,"Linking T cell epitopes to a common linear B cell epitope: A targeting and adjuvant strategy to improve T cell responses," Mol. Immunol., 93: 115-124 (2018).
Madeira, F., et al., "The EMBL-EBI search and sequence analysis tools APIs in 2019," Nucleic Acids Res., 47(W1): W636-W641 (2019).
Liao, Z.-L., et al., "Diepitope multiple antigen peptide of hTERT trigger stronger anti-tumor immune responses in vitro," Int. Immunopharmacol., 16(4): 444-450 (2013).
Ishihara, M., et al., "MAGE-A4, NY-ESO-1 and SAGE mRNA expression rates and co-expression relationships in solid tumours," BMC Cancer., 20(1): 606: 1-8 (2020).
International Search Report of the International Searching Authority, mailed on Dec. 7, 2022, from International Application No. PCT/EP2022/065777, filed on Jun. 9, 2022. 8 pages.
Inderberg Suso, E.M., et al., "hTERT mRNA dendritic cell vaccination: complete response in a pancreatic cancer patient associated with response against several hTERT epitopes," Cancer Immunol Immunother., 60(6):809-818 (2011).

(56) References Cited

OTHER PUBLICATIONS

Inderberg-Suso, E.M., et al., "Widespread CD4+ T-cell reactivity to novel hTERT epitopes following vaccination of cancer patients with a single hTERT peptide GV1001," Oncoimmunology., 1(5): 670-686 (2012).

Gulley, J.L., et al., "Role of Antigen Spread and Distinctive Characteristics of Immunotherapy in Cancer Treatment," J Natl Cancer Inst., 109(4): 1-9 (2017).

Gonzalez-Galarza, F.F., et al., "Allele frequency net database (AFND) 2020 update: gold-standard data classification, open access genotype data and new query tools," Nucleic Acids Res., 48(D1).

Dosset, M., et al., "Telomerase and CD4 T Cell Immunity in Cancer," Cancers, 12(6): E1687: 1-19 (2020).

Bui, H.-H., et al., "Predicting population coverage of T-cell epitope-based diagnostics and vaccines," BMC Bioinformatics., 7(153): 1-5 (2006).

Bernhardt, S.L., et al., "Telomerase peptide vaccination of patients with non-resectable pancreatic cancer: A dose escalating phase I/II study," Br J Cancer., 95(11):1474-1482 (2006).

"Keytruda® (pembrolizumab) for injection, for intravenous use", Whitehouse Station, Merck Sharp & Dohme, Corp, 100 pages.

Zakharia, Y. et al., "A Phase I Clinical Trial Investigating the Therapeutic Cancer Vaccine UV1 in Combination with Pembrolizumab as First-Line Treatment of Patients with Malignant Melanoma (ASCO2021)", Medical Oncology. 2021. 1 page.

Aamdal, E. et al., "Combining a Universal Telomerase Based Cancer Vaccine With Ipilimumab in Patients With Metastatic Melanoma—Five-Year Follow Up of a Phase I/IIa Trial", Frontiers in Immunology, vol. 12, 663865, 2021. 10 pages.

Partial European Search Report mailed Dec. 19, 2023 from European Patent Application No. 23 17 8501.5 filed on Jun. 2, 2017.

Fotin-Mleczek, M., et al., "Highly Potent mRNA Based Cancer Vaccines Represent an Attractive Platform for Combination Therapies Supporting an Improved Therapeutic Effect," Journal of Gene Medicine, 14: 428-439 (2012).

Curran, M.A., et al., "PD-1 and CTLA-4 Combination Blockade Expands Infiltrating T Cells and Reduces T and Myeloid Cells within B16 Melanoma Tumors," PNAS, 107(9): 4275-4280 (2010).

VACCINE IN COMBINATION WITH AN IMMUNE CHECKPOINT INHIBITOR FOR USE IN TREATING CANCER

RELATED APPLICATIONS

This application is continuation of U.S. application Ser. No. 16/306,352, filed on Nov. 30, 2018, which is a § 371 National Phase application of International Application No. PCT/EP2017/063589, filed on Jun. 2, 2017, now International Publication No. WO 2017/207814 A1, published on Dec. 7, 2017, which International Application claims priority to European Application No. 16172760.7, filed on Jun. 2, 2016, all of which are incorporated herein by reference in their entirety.

REFERENCE TO AN ELECTRONIC SEQUENCE LISTING

The contents of the electronic sequence listing (0387.0001US2_PN822210US_sequencelisting.xml; Size: 35 kilobytes; and Date of Creation: Aug. 5, 2022) is herein incorporated by reference in its entirety.

FIELD OF THE INVENTION

The present invention relates to a polypeptide, a nucleic acid molecule, a T-cell receptor, or a T-cell displaying the T-cell receptor, and an immune checkpoint inhibitor for use in medicine. The invention also relates a method of treatment of cancer in a patient. The invention further relates to a composition and a kit suitable for the treatment of cancer.

BACKGROUND OF THE INVENTION

Cancer is a disease characterised by new and abnormal growth of cells within an individual. Cancer develops through a multi-step process involving several mutational events that allow cancer cells to develop, that is to say cells which display the properties of invasion and metastasis.

Numerous approaches have been proposed for the treatment of cancer. One approach is the use of antigenic peptides which comprise fragments of tumour associated antigens (i.e. peptide-based cancer vaccines). Such antigenic peptides, when administered to an individual, elicit an MHC class I or class II restricted T-cell response against cells expressing the tumour associated antigens.

It is to be appreciated that in order for such T-cell responses to occur, the antigenic polypeptide must be presented on an MHC molecule. There is a wide range of variability in MHC molecules in human populations. In particular, different individuals have different HLA alleles which have varying binding affinity for polypeptides, depending on the amino acid sequence of the polypeptides. Thus an individual who has one particular HLA allele may have MHC molecules that will bind a polypeptide of a particular sequence whereas other individuals lacking the HLA allele will have MHC molecules unable to bind and present the polypeptide (or, at least, their MHC molecules will have a very low affinity for the polypeptide and so present it at a relatively low level). Therefore, variability in MHO molecules in the human population means that providing a peptide-based cancer vaccine with broad population coverage is problematic because not all individuals will mount an immune response against a given antigen.

An alternative approach to the treatment of cancer is to target proteins involved in immune checkpoints in order to modulate an individual's immune response to cancer. Immune checkpoint mechanisms that normally down-regulate the immune system in order to prevent excessive and uncontrolled immune responses include cytotoxic T-lymphocyte-associated protein 4 (CTLA-4) and programmed cell death protein 1 (PD-1). CLTA-4 and PD-1 downregulate pathways of T-cell activation and in individuals with cancer, this can result in natural immune responses against cancers being down-regulated. Antibody-mediated blockade of these checkpoints is expected to release the potency of the inhibited immune response and improve survival rates. Blockade of CTLA-4 in a clinical setting, for instance using the anti-CTLA-4 antibodies ipilimumab or tremelimumab, resulted in durable survival benefits in about 20% of patients with metastatic melanoma (McDermott et al. Ann Oncol. 2013 24(10): 2694-2698). Anti-CTLA-4 therapy has also been investigated in other cancers such as non-small cell lung cancer, pancreatic cancer, ovarian cancer, lymphoma, gastric cancer and breast cancer (Postow et al., J Olin Oncol. 2015 33(17):1974-82; Kyi & Postow, FEBS Lett. 2014 588(2):368-76).

The best therapeutic peptide-based cancer vaccines are capable of eliciting cancer specific immune responses in a majority of patients, typically 60-80% (Kyte et al. Clin Cancer Res. 2011 17(13):4568-80; Brunsvig et al. Cancer Immunol Immunother. 2006 55(12):1553-64). However, clinical responses as a result of peptide vaccination are typically seen only in very few patients (Reviewed in Melero et al. Nat Rev Olin Oncol. 2014 11(9):509-24). It was therefore expected that combining peptide-based cancer vaccines with inhibition of immune checkpoints would produce both enhanced immune responses against the vaccine and higher clinical response rates.

However, in a landmark Phase III clinical study combining ipilimumab with a 9-mer gp100 melanoma peptide vaccine, the combination was no better than ipilimumab alone, and the vaccine alone had no protective effect (Hadi et al. N Engl J Med. 2010 363(8):711-23). Very similar results were observed with a combination of another melanoma vaccine, containing three 9-mer peptides derived from Mart 1, gp100 and Tyrosinase, and ipilimumab (Sarnaik et al. Clin Cancer Res, 2011 17(4):896-906). Again no additional clinical benefit was associated with the combination, compared to the result with ipilimumab alone. T cell responses to the individual peptide components of the vaccine were low (0-20%) and not associated with clinical responses. Together the trials included 722 (647+75) patients and thus these data strongly indicated that the administration of an immune checkpoint inhibitor, in particular a CTLA-4 blockade, in combination with peptide-based cancer vaccines does not increase immune responses or result in improved clinical efficacy of such vaccines in humans. This is contrary to what was expected from experiments in mice (Williams et al. Olin Cancer Res. 2013, 19(13) 3545-3555; Met et al. Cancer Lett. 2006 231(2):247-256). The present invention seeks to provide a solution to this problem.

WO2015/095811 relates to methods for the treatment of neoplasia, and more particularly tumours, by administering to a subject a neoplasia vaccine comprising a plurality of neoplasia/tumour-specific neoantigens and at least one checkpoint inhibitor. It is to be appreciated that WO2015/096811 specifically relates to personalised cancer vaccines comprising tumour-specific neoantigens, which are created by the personal mutations found in each patient's tumour. The personalised cancer vaccines disclosed in WO2015/095811 would not be suitable across a broad range of the population. Furthermore, no experimental data on the combination of the personalised cancer vaccines and the checkpoint inhibitors is provided in WO2015/095811 to support the efficacy of this combination in the treatment of cancer. This is significant, given the preponderance of evidence indicating that the administration of an immune checkpoint inhibitor in combination with a peptide-based cancer vaccine does not increase immune responses or result in improved clinical efficacy in humans, as explained above.

WO2015/033140 relates to an immunogenic tumour antigen peptide-derived composition and to the treatment of cancer using the composition. The concept of combining the composition with immunotherapies or immunomodulators (for example, including agents to block immune checkpoints) is disclosed in general terms. However, WO2015/033140 does not provide any experimental data on the combination of the peptide-derived composition with immune checkpoint inhibitors. This is significant, given the preponderance of evidence indicating that the administration of an immune checkpoint inhibitor in combination with a peptide-based cancer vaccine does not increase immune responses or result in improved clinical efficacy in humans, as explained above. Therefore, no enabling disclosure of the combination in the treatment of cancer is provided in WO2015/033140.

WO2016/025647 relates to a method of treating cancer with a combination of IL-2, a therapeutic antibody or fragment thereof, and a cancer vaccine. Example 4 of WO2016/025647 relates to a quadruple combination MSA-IL-2 plus anti-PD-1 antibody plus TA99 (an anti-Trp-1 antibody) plus a cancer vaccine (an amphiphile cancer vaccine targeting Trp-2) in a B16F10 melanoma mouse model. The cancer vaccine is noted on page 84 to elicit a CD8+ T cell response meaning that it was between 8 and 10 amino acids in length. This length of peptide is equivalent to that used in the cancer vaccines of Hodi et al, 2006 and Sarnaik et al. 2011 and which produced no additional clinical benefit in humans when combined with ipilimumab.

Yuan et al. Cancer Immunol Immunother. 2011 August; 60(8):1137-46, reports a study of three ipilimumab-treated patients that had been prevaccinated with either: gp100 DNA; a gp100$^{209-217}$ and tyrosinase$^{369-377}$ peptide vaccine plus GM-CSF DNA; or recombinant human NY-ESO-1 protein. In patient IMF-11, who had been prevaccinated with recombinant human NY-ESO-1 protein, subsequent in vitro immunomonitoring was performed with 20-mer NY-ESO-1 overlapping peptides; however, these peptides were not used in the vaccine itself. The time from vaccination to ipilimumab treatment ranged from 10 months to 2.5 years. There remains a need to provide methods and compositions that provide clinical benefit in humans across a broad range of patients.

WO 2007/113648 relates to uses and compositions comprising an anti-CTLA-4 antibody and at least one therapeutic agent for the treatment of cancer. The combination of an anti-CTLA-4 antibody, CP-675,206, and (whole) tumour antigen is mentioned but there are no experimental data on this combination. For instance, Example 15 relates to administration of an influenza virus vaccine and the CP-675,206 antibody in Rhesus monkeys but no data are provided on the administration of a cancer vaccine derived from a self-antigen in combination with an immune checkpoint inhibitor. This is significant, given the preponderance of evidence indicating that the administration of an immune checkpoint inhibitor in combination with a peptide-based cancer vaccine does not increase immune responses or result in improved clinical efficacy in humans, as explained above.

Foy et al. Cancer Immunol Immunother. 2016 May; 65(5); 537-49, relates to the use of MVA-BN-HER2 poxvirus-based active immunotherapy alone or in combination with CTLA-4 checkpoint blockade in a therapeutic CT26-HER-2 lung metastasis mouse model. MVA-BN-HER2 is a modified vaccinia Ankara-based recombinant vector that encodes a modified form of the human epidermal growth factor receptor 2 (HER-2). The Foy et al, study was performed in mice, where human HER-2 is not a self-antigen. As discussed above in the context of peptide-based cancer vaccines in combination with CTLA-4 blockade, there is a concern that experiments in mice do not necessarily translate into increased immune responses and improved clinical efficacy in humans.

Zanetti Nat Rev Olin Oncol. 2017 February; 14(2):115-128 is a Perspectives opinion article on telomerase reverse transcriptase in anticancer immunotherapy. The discussion encompasses immune checkpoint inhibitors; in particular, in the context of the tumour microenvironment and its role in determining the success of therapeutic vaccination (FIG. 1). In particular, the role of immune checkpoint inhibitors in releasing the brake on (pre-existing) naturally acquired immune responses is discussed and the ability of immune checkpoint inhibitors to restore the activity of exhausted T cells. However, no experimental data are provided to support the discussion which, as mentioned above, is significant given the preponderance of evidence indicating that the administration of an immune checkpoint inhibitor in combination with a peptide-based cancer vaccine does not ease immune responses or result in improved clinical efficacy in humans.

WO 03/086459 relates to methods of promoting or potentiating a secondary or memory immune response using anti-CTLA-4 antibodies. Example 1 relates to a melanoma cell vaccine eliciting a CD4+ and CD8+ response in which a whole cell vaccine expressing GM-CSF was used in Cynomolgus monkeys. Example 5 relates to administration of an anti-CTLA-4 antibody in conjunction with vaccination with two HLA-A*0201-restricted gp100 peptides in humans. These peptides were 9 amino acids in length and were the same peptides (i.e. gp100:209-217(210M) and gp100:280-288(288V)) that were used in the cancer vaccine of Dodi et al, 2010 and which produced no additional clinical benefit in humans when combined with ipilimumab.

WO 2011/101173 discloses various polypeptides from human telomerase reverse transcriptase (hTERT) for the treatment of cancer. There is no disclosure of immune checkpoint inhibitors, There remains a need to provide further anti-cancer treatments.

The present invention seeks to alleviate the at least some of the above problems and, in some aspects, seeks to provide a peptide-based cancer vaccine with broad population coverage that improves clinical response rates in cancer patients when combined with a checkpoint inhibitor.

In this regard it is to be noted that MHC class I molecules are found on the surface of most cells and typically bind polypeptides which are between 8 and 10 amino acid residues in length. MHC class I molecules present polypeptides, which are derived from cytosolic proteins by proteolysis, to CD8+ T cells (also known as cytotoxic T cells or CTLs) in order to elicit a CD8+ T cell response. In contrast, MHC class II molecules are found on the surface of antigen presenting cells and bind polypeptides that are generally longer, typically between 12 and 24 amino acids in length. MHC class II molecules present polypeptides, which are derived from extracellular proteins that have been internalised by endocytosis and digested, to CD4+ T cells (otherwise known as helper T cells or Th cells) in order to elicit a CD4+ T cell response.

The present inventors have made the observation that in the studies described in Hodi et al 2006 and Sarnaik et al. 2011, the peptide-based cancer vaccines comprised short (9-mer) peptides, designed to elicit cytotoxic T cell responses in patients positive for HLA-A2, The present invention arises out of the surprising finding that the combination of a CTLA-4 inhibitor and a peptide-based cancer vaccine comprising at least one peptide that is 12 amino acids or longer (i.e. a "long" peptide) and which is capable of inducing a helper T cell response produces a synergistic effect in the treatment of cancer. This finding led to the surprising realisation that a peptide-based cancer vaccine comprising at least one long peptide of a self-antigen, which is capable of eliciting a helper T cell response in a broad range of patients, in combination with an immune checkpoint inhibitor could result in improved immune responses and improved clinical efficacy in the treatment of cancer across a broad range of the population.

SUMMARY OF THE INVENTION

According to a first aspect of the present invention, there is provided a polypeptide for use in medicine wherein the polypeptide is administered simultaneously, separately or sequentially with an immune checkpoint inhibitor, and
    wherein the polypeptide comprises at least one polypeptide comprising a region of at least 12 amino acids of a self-antigen or a sequence having at least 80% identity to the region.

Preferably, the polypeptide is less than 100 amino acids in length.

In particular, the polypeptide elicits a CD4+ T-cell response.

According to a second aspect of the present invention, there is provided a nucleic acid molecule for use in medicine wherein the nucleic acid molecule is administered simultaneously, separately or sequentially with an immune checkpoint inhibitor, and wherein the nucleic acid molecule comprises a nucleotide sequence encoding at least one polypeptide comprising a region of at least 12 amino acids of a self-antigen or a sequence having at least 80% identity to the region.

According to a third aspect of the present invention, there is provided a T-cell receptor, or a T-cell displaying the T-cell receptor, for use in medicine wherein the T-cell receptor or T-cell is administered simultaneously, separately or sequentially with an immune checkpoint inhibitor, and
    wherein the T-cell receptor or T-cell is specific for a polypeptide consisting of at least 12 amino acids of a self-antigen, or a sequence having at least 80% identity to the polypeptide, when the polypeptide is presented on an MHC molecule.

According to a fourth aspect of the present invention, there is provided an immune checkpoint inhibitor for use in medicine wherein the immune checkpoint inhibitor is administered simultaneously, separately or sequentially with:
    i) a polypeptide comprising at least one polypeptide comprising a region of at least 12 amino acids of a self-antigen or a sequence having at least 80% identity to the region;
    ii) a nucleic acid molecule comprising a nucleotide sequence encoding at least one polypeptide comprising a region of at least 12 amino acids of a self-antigen or a sequence having at least 80% identity to the region;
    iii) a T-cell receptor specific for a polypeptide consisting of at least 12 amino acids of a self-antigen, or a sequence having at least 80% identity to the polypeptide, when the polypeptide is presented on an MHC molecule; or
    iv) a T-cell displaying a T-cell receptor as defined in iii).

Conveniently, the polypeptide under item i) is less than 100 amino acids in length.

Preferably, the polypeptide of the invention, the nucleic acid molecule of the invention, the T-cell or T-cell receptor of the invention or the immune checkpoint inhibitor of the invention is for use in the treatment of cancer.

Preferably, the polypeptide of the invention, the nucleic acid molecule of the invention, the T-cell or T-cell receptor of the invention or the immune checkpoint inhibitor of the invention is for use in the vaccination for cancer.

According to a fifth aspect of the present invention, there is provided a method of treatment of cancer in a patient, comprising the steps of:
    i) inhibiting an immune checkpoint; and
    ii) simultaneously, separately or sequentially administering:
        a) at least one polypeptide comprising a region of at least 12 amino acids of a self-antigen or a sequence having at least 80% identity to the region;
        b) at least one nucleic acid molecule comprising a nucleotide sequence encoding at least one polypeptide comprising a region of at least 12 amino acids of a self-antigen or a sequence having at least 80% identity to the region;
        c) a T-cell receptor specific for a polypeptide consisting of at least 12 amino acids of a self-antigen, or a sequence having at least 80% identity to the polypeptide, when the polypeptide is presented on an MHC molecule; or
        d) a T-cell displaying a T-cell receptor as defined in c).

Advantageously, the at least one polypeptide under item a) is less than 100 amino acids in length.

Conveniently, there is provided a method of vaccination for cancer in a patient as set out in the fifth aspect of the invention.

Preferably, the at least one polypeptide, the T-cell or T-cell receptor in combination with the immune checkpoint inhibitor or the inhibition of the immune checkpoint produce a synergistic effect in the treatment of cancer.

Conveniently, the at least one nucleic acid molecule in combination with the immune checkpoint inhibitor or the inhibition of the immune checkpoint produces a synergistic effect in the treatment of cancer.

Preferably, the at least one polypeptide, the at least one nucleic acid molecule, the T-cell or T-cell receptor in combination with the immune checkpoint inhibitor or the inhibition of the immune checkpoint produce a synergistic effect in the vaccination for cancer.

Advantageously, the polypeptide, the nucleic acid molecule, the T-cell or T-cell receptor in combination with the immune checkpoint inhibitor are for use in generating an accelerated CD4+ T cell immune response.

According to a sixth aspect the present invention, there is provided a composition or kit suitable for the treatment of cancer, comprising:
    i) a) at least one polypeptide comprising a region of at least 12 amino acids of a self-antigen or a sequence having at least 80% identity to the region;

b) at least one nucleic acid molecule comprising a nucleotide sequence encoding at least one polypeptide comprising a region of at least 12 amino acids of a self-antigen or a sequence having at least 80% identity to the region;
c) a T-cell receptor specific for a polypeptide consisting of at least 12 amino acids of a self-antigen, or a sequence having at least 80% identity to the polypeptide, when the polypeptide is presented on an MHC molecule; or
d) a T-cell displaying a T-cell receptor as defined in c) and
ii) an immune checkpoint inhibitor,
wherein the at least one polypeptide, the T-cell or T-cell receptor in combination with the immune checkpoint inhibitor produce a synergistic effect in the treatment of cancer.

Preferably, wherein the at least one nucleic acid molecule in combination with the immune checkpoint inhibitor produces a synergistic effect in the treatment of cancer.

Preferably, the at least one polypeptide, the at least one nucleic acid molecule, the T-cell or T-cell receptor in combination with the immune checkpoint inhibitor produce a synergistic effect in the vaccination for cancer.

Conveniently, the at least one polypeptide under item a) is less than 100 amino acids in length.

Preferably, the at least one polypeptide comprises a region of at least 15, 20, 25 or 30 amino acids of a self-antigen or a sequence having at least 80% identity to the region.

Preferably, the polypeptide comprises a region of at least 15, 20, 25 or 30 amino acids of a self-antigen or a sequence having at least 80% identity to the region.

Conveniently, the self-antigen is a universal tumour antigen, preferably telomerase reverse transcriptase, Top2alpha, survivin or CYP1B1.

Advantageously, the self-antigen is telomerase reverse transcriptase and wherein the at least one polypeptide comprises a polypeptide comprising a sequence of SEQ ID NO, 1 or a sequence having at least 80% sequence identity thereto or an immunogenic fragment thereof comprising at least 12 amino acids.

Conveniently, the self-antigen is telomerase reverse transcriptase and the or the at least one polypeptide comprises:
i) a polypeptide comprising a sequence of SEQ ID NO. 1;
ii) an immunogenic fragment of i) comprising at least 12 amino acids; or
iii) a sequence having at least 80% sequence identity to i) or ii).

According to a seventh aspect of the present invention, there is provided a composition or kit suitable for the treatment of cancer; comprising:
i) at least one polypeptide, wherein the at least one polypeptide comprises a polypeptide comprising a sequence of SEQ. ID NO. 1 or a sequence having at least 80% sequence identity thereto or an immunogenic fragment thereof comprising at least 12 amino acids; and
ii) an immune checkpoint inhibitor.

Conveniently, the at least one polypeptide under item i) comprises:
a) a polypeptide comprising a sequence of SEQ ID NO. 1;
b) an immunogenic fragment of a) comprising at least 12 amino acids; or
c) a sequence having at least 80% sequence identity to a) or b).

Preferably, the at least one polypeptide is a cocktail of polypeptides and wherein the cocktail of polypeptides further comprises:
a polypeptide comprising a sequence of SEQ. ID NO. 2 or a sequence having at least 80% sequence identity thereto or an immunogenic fragment thereof comprising at least 12 amino acids; and optionally,
a polypeptide comprising a sequence of SEQ. ID NO. 3 or a sequence having at least 80% sequence identity thereto or an immunogenic fragment thereof comprising at least 12 amino acids.

Conveniently, the or the at least one polypeptide is a cocktail of polypeptides and wherein the cocktail of polypeptides further comprises:
a polypeptide comprising:
  a) a sequence of SEQ. ID NO. 2;
  b) an immunogenic fragment of a) comprising at least 12 amino acids; or
  c) a sequence having at least 80% sequence identity to a) or b), and optionally,
a polypeptide comprising:
  a) a sequence of SEQ. ID Na 3;
  b) an immunogenic fragment of a) comprising at least 12 amino acids; or
  c) a sequence having at least 80% sequence identity to a) or b).

According to an eighth aspect of the present invention, there is provided a composition or kit suitable for the treatment of cancer, comprising:
i) at least one nucleic acid molecule, wherein the at least one nucleic acid molecule comprises a nucleic acid sequence encoding a polypeptide comprising a primary sequence of SEQ. ID NO. 1 or a secondary sequence having at least 80% sequence identity to the primary sequence or an immunogenic fragment of the primary sequence or the secondary sequence comprising at least 12 amino acids; and
ii) an immune checkpoint inhibitor.

Advantageously, the at least one nucleic acid molecule is a cocktail of nucleic acid molecules, and wherein the cocktail of nucleic acid molecules further comprises:
a nucleic acid molecule comprising a nucleic acid sequence encoding a polypeptide comprising a primary sequence of SEQ. ID NO. 2 or a secondary sequence having at least 80% sequence identity to the primary sequence or an immunogenic fragment of the primary sequence or the secondary sequence comprising at least 12 amino acids; and optionally,
a nucleic acid molecule comprising a nucleic acid sequence encoding a polypeptide comprising a primary sequence of SEQ. ID NO. 3 or a secondary sequence having at least 80% sequence identity to the primary sequence or an immunogenic fragment of the primary sequence or the secondary sequence comprising at least 12 amino acids.

According to a ninth aspect of the present invention, there is provided a composition or kit suitable for the treatment of cancer, comprising:
i) at least one T-cell receptor, or at least one T-cell displaying the T-cell receptor, wherein the T-cell receptor or T-cell is specific for a polypeptide consisting of SEQ. ID NO. 1, or a sequence having at least 80% identity to the polypeptide, when the polypeptide is presented on an MHC molecule; and
ii) an immune checkpoint inhibitor.

Conveniently, the polypeptide under item i) consists of:
a) a sequence of SEQ ID NO. 1;
b) an immunogenic fragment of a) comprising at least 12 amino acids; or
c) a sequence having at least 80% sequence identity to a) or b), when the polypeptide is presented on an MHC molecule.

Preferably, the at least one T-cell receptor is a cocktail of T-cell receptors or the at least one T-cell is a cocktail of T-cells and wherein the cocktail further comprises:
a T-cell receptor, or a T-cell displaying the T-cell receptor, specific for a polypeptide consisting of a sequence of SEQ. ID NO. 2, or a sequence having at least 80% sequence identity thereto, when the polypeptide is presented on an MHC molecule; and optionally,
a T-cell receptor, or a T-cell displaying the T-cell receptor, specific for a polypeptide consisting of a sequence of SEQ. ID NO. 3, or a sequence having at least 80% sequence identity thereto, when the polypeptide is presented on an MHC molecule.

Preferably; the at least one T-cell receptor is a cocktail of T-cell receptors or the at least one T-cell is a cocktail of T-cells and wherein the cocktail further comprises:
a T-cell receptor, or a T-cell displaying the T-cell receptor, specific for a polypeptide consisting of:
a) a sequence of SEQ. ID NO. 2;
b) an immunogenic fragment of a) comprising at least 12 amino acids; or
c) a sequence having at least 80% sequence identity to a) or b), when the polypeptide is presented on an MHC molecule; and optionally,
a T-cell receptor; or a T-cell displaying the T-cell receptor, specific for a polypeptide consisting of:
a) a sequence of SEQ. ID NO. 3
b) an immunogenic fragment of a) comprising at least 12 amino adds; or
c) a sequence having at least 80% sequence identity to a) or b), when the polypeptide is presented on an MHC molecule.

Conveniently, the composition or kit according to the sixth, seventh, eighth or ninth aspect of the invention is suitable for vaccination for cancer.

Advantageously, the immune checkpoint inhibitor is a CTLA-4 inhibitor, a PD-1 inhibitor or a PD-L1 inhibitor, or wherein the inhibition of the immune checkpoint is by administration of a CTLA-4 inhibitor, a PD-1 inhibitor or a PD-L1 inhibitor.

In particular, the immune checkpoint inhibitor is an inhibitor of a member of the CD28CTLA-4 immunoglobulin superfamily.

Conveniently, the CTLA-4 inhibitor is an anti-CTLA-4 antibody or a small molecule CTLA-4 antagonist, wherein the PD-1 inhibitor is an anti-PD-1 antibody or a small molecule PD-1 antagonist, or wherein the PD-L1 inhibitor is an anti-PD-L1 antibody or a small molecule PD-L1 antagonist.

Preferably, the anti-CTLA-4 antibody is: ipilimumab or tremelimumab, wherein the anti-PD-1 antibody is nivolumab or pembrolizumab, or wherein the anti-PD-L1 antibody is MPDL3280A or BMS-936559.

According to a tenth aspect of present invention, there is provided a pharmaceutical composition comprising the composition of the present invention and a pharmaceutically acceptable adjuvant, diluent or excipient and optionally another therapeutic ingredient.

Conveniently, the kit of the present invention, further comprises a pharmaceutically acceptable adjuvant, diluent or excipient and optionally another therapeutic ingredient.

Advantageously, the method of treatment of the present invention, further comprises the administration of a pharmaceutically acceptable adjuvant, diluent or excipient and optionally another therapeutic ingredient.

According to an eleventh aspect of the present invention, there is provided a method of treatment of cancer in a patient comprising administering the composition of the present invention or the pharmaceutical composition of the present invention to the patient.

The terms "polypeptide", "peptide" and "protein" are used interchangeably herein to refer to a polymer of amino acid residues. The terms apply to amino acid polymers in which one or more amino acid residues is a modified residue, or a non-naturally occurring residue, such as an artificial chemical mimetic of a corresponding naturally occurring amino acid, as well as to naturally occurring amino acid polymers.

The term "amino acid" as used herein refers to naturally occurring and synthetic amino acids, as well as amino acid analogues and amino acid mimetics that have a function that is similar to the naturally occurring amino acids. Naturally occurring amino acids are those encoded by the genetic code, as well as those modified after translation in cells (e.g. hydroxyproline, gamma-carboxyglutamate, and O-phosphoserine). The phrase "amino acid analogue" refers to compounds that have the same basic chemical structure (an alpha carbon bound to a hydrogen, a carboxy group, an amino group, and an R group) as a naturally occurring amino acid but have a modified R group or modified backbones (e.g. homoserine, norleucine, methionine sulfoxide, methionine methyl sulphonium). The phrase "amino acid mimetic" refers to chemical compounds that have different structures from but similar functions to naturally occurring amino acids.

The term "fragment" as used herein in relation to a polypeptide means a consecutive series of amino acids that form part of the polypeptide. An "immunogenic fragment" of a polypeptide is a fragment as previously defined which is capable of eliciting an immune response, such as a T-cell response, when administered to an individual. In some embodiments an "immunogenic fragment" of a polypeptide is a fragment as previously defined which is capable of eliciting an MHC class II restricted immune response.

The terms "gene", "polynucleotides", and "nucleic acid molecules" are used interchangeably herein to refer to a polymer of multiple nucleotides. The nucleic acid molecules may comprise naturally occurring nucleic acids or may comprise artificial nucleic acids such as peptide nucleic acids, morpholin and locked nucleic acid as well as glycol nucleic acid and threose nucleic acid.

The term "nucleotide" as used herein refers to naturally occurring nucleotides and synthetic nucleotide analogues that are recognised by cellular enzymes.

The term "cancer" as used herein refers to a group of diseases that are characterised by new and abnormal and/or uncontrolled proliferation of cells in an individual. Cancer cells have the capacity to invade adjacent tissues and/or to spread to other sites in the body (i.e. the cancer cells are capable of metastasis).

The term "treatment" as used herein refers to any partial or complete treatment and includes: inhibiting the disease or symptom, i.e. arresting its development; and relieving the disease or symptom, i.e. causing regression of the disease or symptom.

The term "self-antigen" as used herein refers to an antigen that is derived from a naturally-occurring protein within the human body. Under normal conditions, the immune system does not react to self-antigens due to negative selection of T cells in the thymus. However, in an individual with cancer, self-antigens may be recognised as foreign by the immune system (for example, as a result of the cancer cell overexpressing the protein from which the self-antigen is derived or expressing it inappropriately given the tissue in which the cancer developed) and a T cell immune response is mounted against the self-antigen. In some embodiments, the self-antigen may be referred to as a "tumour-associated antigen" i.e. an antigen associated with a cancer cell as well as a normal cell. An example of a self-antigen is telomerase reverse transcriptase.

The term "universal tumour antigen" as used herein refers to an antigen that is expressed in (nearly) all tumours, such as in at least 80%, 85% or 90% of all tumour types. In some embodiments, the universal tumour antigen is directly involved in the malignant phenotype of the tumour. Examples of a universal tumour antigen include telomerase reverse transcriptase, Top2alpha, survivin and CYP1B1.

The term "T-cell" (also known as "T lymphocyte") as used herein refers to a cell that is capable of recognising a specific antigen and which comprises a cell surface T-cell receptor. The term "T-cell" comprises different types of T cell, such as: CD4+ T cells (also known as helper T cells or Th cells), CD8+ T cells (also known as cytotoxic T cells or CTLs), memory T cells and regulatory T cells (Tregs).

The term "the T-cell receptor" as used herein refers to an antigen receptor of the T-cell. In some embodiments, the T-cell receptor recognises (i.e. binds to) a polypeptide when presented by an MHC molecule.

The term "a T-cell displaying the T-cell receptor" as used herein refers to a T-cell that comprises the T-cell receptor on its cell surface. In some embodiments, the T-cell receptor is responsible for recognising (i.e. binding to) a polypeptide when presented by an MHC molecule. In some embodiments, the binding of the T-cell receptor to the polypeptide when presented by the MHC molecule results in activation of the T-cell displaying the T-cell receptor. T cell activation can be measured using T-cell response assays and ELISPOT assays as described herein.

The term "the T-cell receptor or T-cell is specific for a polypeptide" as used herein refers to a T-cell receptor or a T cell comprising the T-cell receptor that is capable of recognising (i.e. binding to) the polypeptide when presented on an MHC molecule. In some embodiments, the polypeptide to which the T-cell receptor (or the T-cell displaying the T-cell receptor) is specific, is of a length that is longer than that which would normally be accommodated on an MHC molecule. In these embodiments, the term "the T-cell receptor or T-cell is specific for a polypeptide" as used herein refers to the recognition by the T-cell receptor or T-cell of an immunogenic fragment of the polypeptide when presented on the MHC molecule. In some embodiments, the binding of the T-cell receptor or T-cell to the polypeptide to which it is specific results in activation of a T-cell. T cell activation can be measured using T-cell response assays and ELISPOT assays as described herein.

The term "MHC molecule" as used herein refers to a protein structure which assembles with a polypeptide and which is capable of displaying the polypeptide at a cell surface to a T-cell. MHC molecules are encoded by genes within the major histocompatibility complex. In some embodiments, the term "MHC molecule" refers to an MHC class I molecules and/or an MHC class II molecule.

The term "immune checkpoint" as used herein refers to any point at which an immune response is limited. Immune checkpoints are inhibitory pathways that slow down or stop immune reactions and prevent excessive tissue damage from uncontrolled activity of immune cells. Examples of an "immune checkpoint" include the cytotoxic T-lymphocyte-associated protein 4 (CTLA-4) checkpoint and the programmed cell death protein 1 (PD-1) checkpoint.

The term "immune checkpoint inhibitor" as used herein refers to any compound, substance or composition (e.g. any small molecule, chemical compound, antibody, nucleic acid molecule, polypeptide, or fragments thereof, a vaccine or viral vaccine) that is capable of down-regulating or blocking an immune checkpoint allowing more extensive immune activity. The term "checkpoint inhibitor" is used interchangeably herein with "immune checkpoint inhibitor". In some embodiments, the immune checkpoint inhibitor is an antibody that specifically binds to a protein involved in the immune checkpoint pathway thereby disrupting and down-regulating the overall activity of the immune checkpoint. Examples of such an immune checkpoint inhibitor include an anti-CTLA-4 antibody (such as ipilimumab, tremelimumab or AGEN-1884) and an anti-PD-1 antibody (such as nivolumab or pembrolizumab). In alternative embodiments; the immune checkpoint inhibitor is a small molecule antagonist that interferes with and/or inhibits the activity of a protein involved in the immune checkpoint pathway and thereby down-regulates the overall activity of the immune checkpoint. In a preferred embodiment, the small molecule antagonist targets the CTLA-4 and/or PD-1 proteins in order to down-regulate the CTLA-4 and/or PD-1 checkpoints (i.e. the small molecule antagonist is a small molecule CTLA-4 antagonist or a small molecule PD-1 antagonist). In additional embodiments, the immune checkpoint inhibitor is targeted at another member of the CD28CTLA4 Ig superfamily such as BTLA, LAG3, ICOS, PDL1 or KIR (Page et al., Annual Review of Medicine 65:27 (2014)). In further additional embodiments, the immune checkpoint inhibitor is targeted at a member of the TNFR superfamily such as CD40, OX40, CD137, GITR, CD27 or TIM-3. In a further embodiment, the immune checkpoint inhibitor targets Indoleamine 2,3-dioxygenase (IDO). In some cases targeting an immune checkpoint is accomplished with an inhibitory antibody or similar molecule. In other cases, it is accomplished with an agonist for the target; examples of this class include the stimulatory targets OX40 and GITR.

In a preferred embodiment, the immune checkpoint inhibitor targets an immune checkpoint that is involved in the regulation of a T-cell. In some embodiments, the immune checkpoint that is targeted is a negative regulator of T-cell activity; thus the action of the immune checkpoint inhibitor allows for more extensive T-cell activity. As discussed above, in some embodiments, the immune checkpoint inhibitor targets a member of the CD28CTLA4 immunoglobulin (Ig) superfamily. Proteins in the immunoglobulin superfamily possess an immunoglobulin domain (also known an immunoglobulin fold) which is a characteristic beta-sheet fold. CTLA-4, PD-1 and PD-L1 are examples of members of the CD28CTLA4 Ig superfamily.

The term "inhibiting an immune checkpoint" as used herein refers to down-regulating or blocking an immune checkpoint in order to allow more extensive immune activity. In some embodiments, inhibiting an immune checkpoint is achieved using at least one of the immune checkpoint inhibitors described above.

The term "synergistic effect in the treatment of cancer" as used herein refers to presence of at least one of the following combination of factors in patients who have been administered a peptide-based (or a nucleic acid molecule-based) cancer vaccine and a checkpoint inhibitor in comparison with a control (for example, patients who have been administered the peptide-based cancer vaccine without the checkpoint inhibitor; or alternatively, patients who have been administered the checkpoint inhibitor without the peptide-based cancer vaccine).

1. A reduction in the time required by the immune system of the patients to mount a measurable immune response to the peptide(s) of the vaccine. In other words, an accelerated CD4+ T cell immune response is generated.
2. The mounting of a strong immune response to the peptide(s) of the vaccine by the patients. In one embodiment, a "strong immune response" as used herein refers to, when across an average of 10 patients, the mean peak immune response is an SI of at least 17, preferably at least 19.
3. An improved clinical outcome in the patients.

In some embodiments, the term "synergistic effect in the treatment of cancer" refers to the presence of at least two of said factors or all three of said factors in patients. In one embodiment, an additional factor, namely, the induction of a broad immune response (i.e. the mounting of an immune response against 2, 3 or more vaccine components), is further evidence of a synergistic effect in the treatment of cancer. In a preferred embodiment, immune responses are measured by a T cell response assay (proliferation by 3H-thymidine incorporation) using patient blood samples as explained in the Materials and Methods section herein. A specific T-cell response is considered positive if the peptide response is at least 3 times the background (Stimulation Index, SI≥3). In one embodiment, a synergistic effect is provided when; across an average of ten patients, over 50% exhibit a positive immune response 7 weeks after the first administration of the peptide vaccine; and the mean peak immune response is an SI of at least 17, preferably at least 19. In some embodiments, an improved clinical outcome is a partial or complete response (also known as partial or complete remission) or stable disease. A complete response refers to the disappearance of detectable tumour or cancer in the body in response to treatment; a partial response refers to a decrease in tumour size, or in the extent of cancer in the body, in response to treatment; and stable disease means that tumour or cancer in the body is neither decreasing nor increasing in extent or severity.

The term "generating an accelerated CD4+ T cell immune response" as used herein refers to a reduction in the amount of time required by the immune system to mount a measurable CD4+ T cell immune response. In one embodiment, a response time refers to the time from: the start of vaccination; to: the expansion of vaccine specific CD4+ T-cells to a level defining a positive vaccine response. In this embodiment, an accelerated CD4+ T cell response is defined as T2<T1 where T1 is the response time of the vaccine alone and T2 is the response time of the combined treatment of the vaccine and the immune checkpoint inhibitor. In one embodiment, the vaccine comprises a polypeptide of the invention; in an alternative embodiment, the vaccine comprises a nucleic acid molecule of the invention.

In certain embodiments, where the vaccine is a clinical vaccine, T1 and T2 refer to the average values in a treated population. In one embodiment, T1 and T2 refer to the average values across 10 or more patients. The level defining a positive immune response is dependent on the assay used. In one embodiment, it is based on a detection threshold; in an alternative embodiment, it is a pre-defined value. In certain embodiments, the assay used to measure the immune response is a T cell proliferation assay (proliferation by 3H-thymidine incorporation) as described herein. In one embodiment, the level defining a positive immune response is pre-defined to a stimulation index (SI) of 3 (SI≥3), It is to be understood that this level is higher than the detection threshold and is selected, in certain embodiments, to represent a potentially clinically relevant immune response. In other embodiments, the SI is less than or higher than 3. In one embodiment, the SI is 2 or 4.

In one embodiment, T1 as defined above is the number of weeks to when 50% or more of patients treated with the vaccine alone have a positive immune response; and T2 is the number of weeks to when 50% or more of patients treated with the combination of the vaccine and the immune checkpoint inhibitor have a positive immune response. In one embodiment, an accelerated immune response refers to a 60% decrease in T2 compared with T1 (for example, T2 is 4 weeks as compared with T1 which is 10 weeks). In other embodiments, an accelerated CD4+ immune response refers to a 55%, 50%, 45%, 40%, 35% or 30% decrease in T2 as compared with T1. Samples are collected at discrete time points and so, in some embodiments, calculation of T1 and T2 requires interpolation.

The term "telomerase reverse transcriptase" (TERT) as used herein refers to the catalytic component of the telomerase holoenzyme complex whose main activity is the elongation of telomeres by acting as a reverse transcriptase that adds simple sequence repeats to chromosome ends by copying a template sequence within the RNA component of the telomerase enzyme. In some embodiments, the term telomerase refers to the human telomerase reverse transcriptase protein (hTERT). The full-length hTERT sequence is set out in GenBank accession no. AF015950.1 and is set forth in SEQ ID NO. 6.

In this specification, the percentage "identity" between two sequences is determined using the BLASTP algorithm version 2.2.2 (Altschul, Stephen F., Thomas L. Madden, Alejandro A. Schäffer, Jinghui Zhang, Zheng Zhang, Webb Miller, and David J. Lipman (1997), "Gapped BLAST and PSI-BLAST: a new generation of protein database search programs", Nucleic Acids Res, 25:3389-3402) using default parameters. In particular, the BLAST algorithm can be accessed on the internet using the URL http://www.ncbi.nlm.nih.gov/blast/.

DETAILED DESCRIPTION OF THE INVENTION

Figure 1:
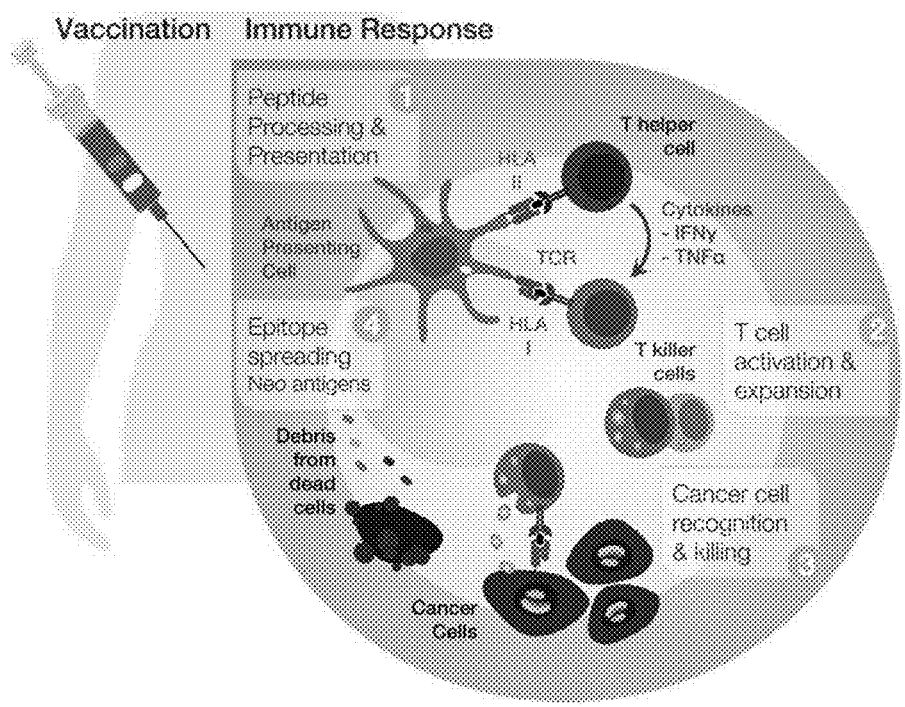
FIG. 1 is a schematic showing the mechanism by which an embodiment of the present invention elicits an immune response.

The present invention provides a kit for the treatment of cancer. The kit comprises two components. In a first embodiment, the first component is at least one polypeptide of a self-antigen, wherein the polypeptide is at least 12 amino acids in length. The second component is an immune checkpoint inhibitor.

Polypeptides

The first component of the kit for the treatment of cancer is at least one polypeptide of a self-antigen.

A self-antigen is an antigen that is derived from a naturally-occurring protein within the human body. Cancer cells may express certain self-antigens at a higher level than normal cells or the self-antigen may be expressed inappropriately given the tissue in which the cancer cell developed. These self-antigens can be regarded as "tumour-associated antigens" and thus represent a potential target for cancer therapy. It is preferred that the self-antigen is a universal tumour antigen, which is an antigen expressed in (nearly) all human tumours. It is to be appreciated that certain tumour associated antigens are both self-antigens and universal tumour antigens. Cancer is a heterogeneous disease and there is high degree of diversity between different types of cancer as well as between individuals with the same type of cancer. By targeting universal tumour antigens, the applicability of the cancer therapy is improved across the patient population (i.e. within and between cancer types).

In a first embodiment of the invention, the self-antigen is the telomerase reverse transcriptase subunit ("TERT" or "hTERT" for humans) of the telomerase enzyme. The telomerase enzyme is a "self-protein", that is to say, it is a naturally-occurring protein in the human body. Furthermore, it has been observed that the telomerase enzyme is activated in the vast majority of all human tumours. In view of this, polypeptides of hTERT are regarded as both self-antigens and universal tumour antigens.

Telomerase is an enzyme that has the function of replicating the 3' end of the telomere regions of linear DNA strands in eukaryotic cells as these regions cannot be extended by the enzyme DNA polymerase in the normal way. The telomerase enzyme comprises a telomerase reverse transcriptase subunit ("TERT" or "hTERT" for humans) and telomerase RNA. By using the telomerase RNA as a template, the telomerase reverse transcriptase subunit adds a repeating sequence to the 3' end of chromosomes in eukaryotic cells in order to extend the 3' end of the DNA strand. The full-length hTERT sequence is set out in GenBank accession no. AF015950.1 and is set forth in SEQ ID NO. 6.

Telomerase is expressed in certain normal tissue such as stem cells in the bone marrow and gastrointestinal tract. However, it has been observed that the telomerase enzyme is activated in the vast majority of all human tumours (for example, Kim et al., Science. 1994 266(5193):2011-5; Shay & Wright, FEBS Lett. 2010 584(17):3819-25). It is believed that telomerase is activated in the vast majority of human tumours because; without the expression of the telomerase enzyme, the telomeres of cells are gradually lost, and the integrity of the chromosomes decline with each round of cell division of a cell, which ultimately results in apoptosis of the cells. Thus, expression of the telomerase enzyme is generally necessary for a cancer cell to develop because without such expression, programmed cell death will usually occur by default. In view of the role of telomerase activation in cancer, polypeptides from hTERT are regarded as universal tumour antigens.

In alternative embodiments, the self-antigen and/or universal tumour antigen is from a protein other than hTERT. In one embodiment, the self-antigen and/or universal tumour antigen is selected from: topoisomerase II alpha (Top2alpha), survivin or cytochrome P450 181 (CYP1B1) (Park et al., Cancer Immunol Immunother. 2010 (5):747-57; Sørensen et al., Cancer Biol Ther. 2008 7(12):1885-7; Wobser et al., Cancer Immunol Immunother. 2006 55(10):1294-8; Gribben et al., Clin Cancer Res. 2005 11(12):4430-6). In some embodiments, the at least one polypeptide is a cocktail (i.e. a mixture) of polypeptides. In the first embodiment, the cocktail of polypeptides comprises at least two different polypeptides of the hTERT protein. However, in some embodiments, the cocktail of polypeptides comprises at least two different polypeptides selected from any one of the different self-antigens and/or universal tumour antigens. In one embodiment, the cocktail of polypeptides comprises at least two different polypeptides selected from any one of: hTERT, Top2alpha, survivin or CYP1B1.

The at least one polypeptide of a self-antigen in the first component of the kit for the treatment of cancer is at least 12 amino acids in length.

It is to be appreciated that different lengths of polypeptide elicit different T cell responses. More specifically, in order to elicit a CD8+ T-cell response, the polypeptide must be presented on MHC class I molecules which will typically only bind polypeptides which are between 8 and 10 amino acid residues in length. On the other hand, in order to elicit a CD4+ T-cell response, it is necessary for the polypeptide to be presented on an MHC class II molecule for which the polypeptides may generally be longer, typically between 12 and 24 amino acid residues in length. Therefore, the at least one polypeptide of a self-antigen or universal tumour antigen is capable of eliciting a CD4+ T-cell response (i.e. a helper T cell response) because it is of a longer length (i.e. at least 12 amino acids in length).

It is preferred that the at least one polypeptide of the self-antigen is equal to or at least 15 amino acids in length. In some embodiments, the at least one polypeptide of the self-antigen is equal to or at least 16, 17, 18, 19, 20, 25 or 30 amino acids in length. In some embodiments, the at least one polypeptide is less than 100 amino acids in length preferably less than 50, 40 or 30 amino acids in length.

In embodiments where the self-antigen is telomerase (more specifically, hTERT), it is preferred that the polypeptide comprises sequences from SEQ. ID NOS. 1 to 5. It is particularly preferred that the polypeptide comprises the sequence of SEQ. ID NOS. 1, 2 or 3. It is especially preferred that the polypeptide consists of the sequence of SEQ. ID NOS. 1, 2 or 3. It is to be understood that such polypeptides are capable of eliciting a CD4+ T-cell response (i.e. a helper T cell response) because each of the polypeptides is at least 12 amino acids in length. SEQ. ID NO: 1 is 30 amino acids in length; SEQ. ID NOS: 2, 3 and 4 are 15 amino acids; and SEQ ID NO: 5 is 16 amino acids in length.

In other embodiments, there are provided immunogenic fragments of the aforementioned polypeptides, which comprise at least 12 amino acids of SEQ. ID NOS: 1 to 5. In one embodiment, the immunogenic fragments comprise at least 12, 13 or 14 amino acids of SEQ. ID NOS. 1 to 5. In another embodiment, the immunogenic fragments comprise at least 15, 16, 17, 18, 19, 20 or 25 amino acids of SEQ. ID NO, 1. In certain embodiments, the cocktail of polypeptides comprises immunogenic fragments of SEQ. ID NOS. 1 to 5, wherein the immunogenic fragments comprise at least 12 amino acids. Exemplary immunogenic fragments include those set out in SEQ ID NOS. 7 to 38. It is to be appreciated that the polypeptides of SEQ. ID NOS. 7 to 23 and 24 to 30 are all immunogenic fragments of the polypeptide of SEQ. ID NO. 1. The polypeptides of SEQ. ID NOS. 31 to 34 are all immunogenic fragments of the polypeptide of SEQ. ID NO, 2. The polypeptides of SEQ. ID NOS. 35 to 38 are all immunogenic fragments of the polypeptide of SEQ. ID NO. 3.

In further embodiments, the at least one polypeptide provided does not have exact sequence identity to one of the aforementioned polypeptides. Instead, the polypeptide has at least 80% sequence identity to the polypeptide set out above. It is particularly preferred that the sequence has at least 90%, 95% or 99% sequence identity to that set out above. It is also preferred that any addition or substitution of amino acid sequence results in the conservation of the properties of the original amino acid side chain. That is to say the substitution or modification is "conservative".

Conservative substitution tables providing functionally similar amino acids are well known in the art. Examples of properties of amino acid side chains are hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side chain (S, T, Y); a sulphur atom containing side-chain (C, M); a carboxylic acid and amide containing side-chain (D, N, E, Q); a base containing side-chain (R, K, H); and an aromatic containing side-chain (H, F, Y, W). In addition, the following eight groups each contain amino acids that are conservative substitutions for one another (see e.g. Creighton; Proteins (1984):
1) Alanine (A), Glycine (G);
2) Aspartic acid (D), Glutamic acid (E);
3) Asparagine (N), Glutamine (Q)
4) Arginine (R), Lysine (K)
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M).

In some embodiments, the sequence of the at least one polypeptide is altered in order to change (e.g. increase) the binding affinity of a polypeptide to an MHC class II molecule of a particular HLA allele. In other embodiments, the polypeptide has further amino acids, in addition to those set out above, at the N- and/or C-terminal thereof. Such additional amino acids can also be used to alter (e.g. increase) the binding affinity of a polypeptide to an MHC molecule.

It is to be understood that the polypeptide is not limited to having a sequence corresponding to a fragment of the self-antigen. That is to say, in some embodiments, the polypeptide comprises additional amino acid sequences at the N-terminal and/or C-terminal, in addition to the region corresponding to the self-antigen. However, the region corresponding to the self-antigen (i.e. at least 80%, 90%, 95% or 99% identical to as set out above) is at least 12 amino acids in length.

In some further embodiments of the present invention, the at least one polypeptide is linked (e.g. covalently) to other substances, while retaining its capability of inducing a CD4+ T-cell response. Such other substances include lipids, sugar and sugar chains, acetyl groups, natural and synthetic polymers and the like. The at least one polypeptide, in certain embodiments, contains modifications such glycosylation, side chain oxidation or phosphorylation.

In some embodiments, the at least one polypeptide is a cocktail of polypeptides, such as a cocktail of polypeptides from the same self-antigen or from two or more different self-antigens. In one embodiment, the cocktail comprises at least 2 or at least 3 different polypeptides of the self-antigen. It is particularly preferred that in the cocktail of polypeptides, the polypeptides in the cocktail are capable of being bound by MHC class H molecules of more than one HLA allele. It is also to be understood that in some embodiments the cocktail comprises more than two polypeptides having different sequences (e.g. 3, 4 or 5 polypeptides).

It is preferred that the cocktail of polypeptides comprises polypeptides of the hTERT protein. It is preferred that the polypeptides in the cocktail comprise sequences from at least 2 different polypeptides comprising sequences from SEQ. ID NOS. 1 to 5. It is particularly preferred that the polypeptides in the cocktail comprise the sequence of SEQ. ID NOS. 1, 2 and 3. It is especially preferred that the polypeptides in the cocktail consist of the sequences of SEQ. ID NOS. 1, 2 and 3.

In some embodiments, the at least one polypeptide is produced by conventional processes known in the art. Alternatively, the at least one polypeptide is a fragment of a protein produced by cleavage, for example, using cyanogen bromide, and subsequent purification. Enzymatic cleavage may also be used. In further embodiments, the at least one polypeptide is in the form of a recombinant expressed polypeptide. For example, a suitable vector comprising a polynucleotide encoding the polypeptide in an expressible form (e.g. downstream of a regulatory sequence corresponding to a promoter sequence) is prepared and transformed into a suitable host cell. The host cell is then cultured to produce the polypeptide of interest. In other embodiments, the at least one polypeptide is produced in vitro using in vitro translation systems.

Nucleic Acid Molecules

In a second embodiment of the present invention, there is provided a nucleic acid molecule comprising a nucleotide sequence encoding a polypeptide as set out above.

In embodiments where the self-antigen is telomerase, it is preferred that the nucleic acid molecule comprises a nucleotide sequence encoding a polypeptide comprising sequences from SEQ. ID NOS. 1 to 5. It is particularly preferred that the nucleic acid molecule comprises a nucleotide sequence encoding a polypeptide comprising the sequence of SEQ. ID NOS. 1, 2 or 3. It is especially preferred that the nucleic acid molecule comprises a nucleotide sequence encoding a polypeptide consisting of the sequence of SEQ. ID NOS. 1, 2 or 3.

In some embodiments, there is provided a cocktail (that is to say a mixture) of nucleic acid molecules such as a cocktail of nucleic acid molecules comprising nucleotide sequences encoding polypeptides from the same self-antigen or from two or more different self-antigens. In one embodiment, the cocktail comprises at least 2 or at least 3 different nucleic acid molecules comprising nucleotide sequences encoding polypeptides of the self-antigen. It is particularly preferred that in the cocktail of nucleic acid molecules, the encoded polypeptides are capable of being bound by MHC class II molecules of more than one HLA allele. It is also to be understood that in some embodiments the cocktail comprises more than two nucleic acid molecules encoding different polypeptide sequences (e.g. 3, 4 or 5 nucleic acid molecules).

It is preferred that the cocktail of nucleic acid molecules comprise nucleotide sequences encoding polypeptides of the hTERT protein. It is preferred that the encoded polypeptide sequences in the cocktail comprise sequences from at least 2 different polypeptides comprising sequences from SEQ. ID NOS. 1 to 5. It is particularly preferred that the encoded polypeptides in the cocktail comprise the sequence of SEQ. ID NOS. 1, 2 and 3. It is especially preferred that the encoded polypeptides in the cocktail consist of the sequences of SEQ. ID NOS. 1, 2 and 3.

In alternative variants, the sequence of the encoded polypeptide is not identical to that aforementioned but instead has at least 80%, 90%, 95% or 99% sequence identity thereto. In any case, the encoded polypeptide is less than 100 amino acids in length preferably less than 50, 40 or 30 amino acids in length.

In some further embodiments of the present invention, the or each nucleic acid molecule is linked (e.g. covalently) to other substances.

It is to be appreciated that, owing to the degeneracy of the genetic code, nucleic acid molecules encoding a particular polypeptide may have a range of polynucleotide sequences. For example, the codons GCA, GCC, GCG and GCT all encode the amino acid alanine.

The nucleic acid molecules may be either DNA or RNA or derivatives thereof.

T-Cell Receptor or T-Cell

In a third embodiment of the present invention, there is provided a T-cell receptor, or a T-cell displaying the T-cell receptor, which is specific for a polypeptide as set out above, when the polypeptide is presented on an MHC molecule.

As set out above, the polypeptide of the present invention comprises a region of at least 12 amino acids of a self-antigen. Polypeptides of this length are presented on MHC class II molecules. Therefore, the T-cell receptor, or the T-cell displaying the T-cell receptor is capable of recognising and binding to a polypeptide when presented on an MHC class II molecule. MHC class II molecules typically bind polypeptides that are between 12 and 24 amino acids in length. In embodiments where the T-cell receptor, or the T-cell displaying the T-cell receptor, is described as specific for a polypeptide that is longer than 12 to 24 amino acids in length, it is to be understood that an immunogenic fragment of the polypeptide is presented on the MHC molecule.

In embodiments where the self-antigen is telomerase (hTERT), it is preferred that the T-cell receptor, or the T-cell displaying the T-cell receptor, is specific for a polypeptide consisting of a sequence selected from SEQ ID NOS. 1 to 5, or an immunogenic fragment thereof consisting of at least 12 amino acids, when the polypeptide or the immunogenic fragment thereof is presented on an MHC molecule. It is particularly preferred that the T-cell receptor, or the T-cell displaying the T-cell receptor, is specific for a polypeptide consisting of the sequence of SEQ ID NO. 1, 2 or 3, or an immunogenic fragment thereof consisting of at least 12 amino acids, when the polypeptide or the immunogenic fragment thereof is presented on an MHC molecule.

In some embodiments, there is provided a cocktail (i.e. a mixture) of T-cell receptors, or a cocktail of T-cells displaying the T-cell receptors. That is to say, the cocktail comprises different T-cell receptors, or T-cells displaying the different T-cell receptors, each of which is specific for a different polypeptide, when presented on an MHC molecule.

In one embodiment, the cocktail of different T-cell receptors, or the cocktail of T-cells displaying the different T-cell receptors is specific for different polypeptides from the same self-antigen, when each polypeptide is presented on an MHC molecule, or alternatively, is specific for different polypeptides from two or more different self-antigens, when each polypeptide is presented on an MHC molecule. In one embodiment, the cocktail of different T-cell receptors, or the cocktail of T-cells displaying the different T-cell receptors, is specific for at least 2 or at least 3 different polypeptides of a self-antigen, when each polypeptide is presented on an MHC molecule. That is to say, in some embodiments, the cocktail is specific for more than 2 or more than 3 polypeptides having different sequences, when each polypeptide is presented on an MHC molecule (e.g. 3, 4, or 5 polypeptides). It is particularly preferred that the cocktail of different T-cell receptors, or the cocktail of T-cells displaying the different T-cell receptors, is specific for polypeptides capable of being bound and presented by MHC class I and/or class II molecules of more than one HLA allele.

It is preferred that the cocktail of T-cell receptors, or the cocktail of T-cells displaying the T-cell receptors, is specific for different polypeptides of the hTERT protein, when each polypeptide is presented on an MHC molecule.

It is preferred that the polypeptides to which the cocktail of T-cell receptors, or the cocktail of T-cells displaying the T-cell receptors, are specific when presented on an MHC molecule, consist of sequences from at least 2 different polypeptides comprising sequences from SEQ. ID NOS. 1 to 5. It is particularly preferred that the polypeptides to which the cocktail of T-cell receptors, or the cocktail of T-cells displaying the T-cell receptors, are specific when presented on an MHC molecule, consist of the sequence of SEQ. ID NOS. 1, 2 and 3. It is especially preferred that the polypeptides to which the cocktail of T-cell receptors, or the cocktail of T-cells displaying the T-cell receptors, are specific when presented on an MHC molecule, consist of the sequences of SEQ. ID NOS. 1, 2 and 3.

In some embodiments, a polypeptide to which the cocktail of T-cell receptors, or the cocktail of T-cells displaying the T-cell receptors, is specific is an immunogenic fragment of that polypeptide, and the immunogenic fragment is presented on the MHC molecule. It is to be understood that certain aforementioned polypeptides, such as SEQ ID NO. 1, are longer than would normally be accommodated on an MHC class II molecule. Therefore, in embodiments in which a T-cell receptor, or a T-cell displaying the T-cell receptor, or a cocktail thereof, is described as specific for a polypeptide comprising or consisting of the sequence of SEQ ID NO. 1, it is to be understood that an immunogenic fragment, comprising at least 12 amino acids of SEQ ID NO. 1, is presented on the MHC molecule.

In alternative variants, the sequence of the polypeptide to which the or each T-cell receptor, or the or each T-cell displaying the T-cell receptor, is specific when bound to an MHC molecule is not identical to that aforementioned but instead has at least 80%, 90%, 95% or 99% sequence identity thereto, provided that the polypeptide is still capable of being presented by the MHC molecule.

Immune Checkpoint Inhibitor

The second component of the kit for the treatment of cancer is an immune checkpoint inhibitor.

In the present invention, an immune checkpoint inhibitor is any compound, substance or composition (e.g. any small molecule chemical compound, antibody, nucleic acid molecule, or polypeptide, or fragments thereof) that is capable of down-regulating or blocking an immune checkpoint to allow more extensive immune activity. It is preferred that the immune checkpoint inhibitor targets the CTLA-4 checkpoint and/or the PD-1 checkpoint. In additional embodiments, the immune checkpoint inhibitor is targeted at another member of the CD28CTLA-4 Ig superfamily such as BTLA, LAG3, ICOS, PDL1 or KIR (Page et al., Annual Review of Medicine 65:27 (2014)). In further additional embodiments, the immune checkpoint inhibitor is targeted at a member of the TNFR superfamily such as CD40, OX40, CD137, GITR, CD27 or TIM-3. In a further embodiment, the immune checkpoint inhibitor targets Indoleamine 2,3-dioxygenase (100).

In some embodiments, targeting an immune checkpoint is accomplished with an inhibitory antibody, or antigen-binding fragment thereof or a similar molecule. Examples of such suitable therapeutic agents are shown in Table 1 and Table 2 below. In a preferred embodiment, the immune checkpoint inhibitor is an antibody that specifically binds to a protein involved in the immune checkpoint pathway thereby disrupting and down-regulating the overall activity of the immune checkpoint. It is particularly preferred that the immune checkpoint inhibitor is an anti-CTLA-4 antibody or an anti-PD-1 antibody. It is especially preferred that the anti-CTLA-4 antibody is ipilimumab or tremelimumab; and that the anti-PD-1 antibody is nivolumab or pembrolizumab.

In some embodiments, the immune checkpoint inhibitor is a small molecule antagonist that interferes with and/or inhibits the activity of a protein involved in the immune checkpoint pathway and thereby down-regulates the overall activity of the immune checkpoint. In a preferred embodiment, the small molecule antagonist targets the CTLA-4 and/or PD-1 proteins in order to down-regulate the CTLA-4 and/or PD-1 checkpoints (i.e. the small molecule antagonist is a small molecule CTLA-4 antagonist or a small molecule PD-1 antagonist).

In a further embodiment, the immune checkpoint inhibitor is an anti-PD-L1 antibody (i.e. an antibody that specifically binds to PD-L1, which is an endogenous ligand of PD-1). It is preferred that the anti-PD-L1 antibody is BMS-936559 or MPDL3280A. In an alternative embodiment, targeting an immune checkpoint is accomplished with an agonist for the target; examples of this class include the stimulatory targets OX40 and GITR.

TABLE 1

Other immunotherapeutic agents in development

| Target | Name | Indication(s) |
|---|---|---|
| B7.1 | Galiximab | Lymphoma |
| B7H3 | MGA271 | Solid tumours |
| LAG3 | IMP321 | Solid tumours |
| | BMS-986016 | Solid tumours |
| CD137 | BMS-663513 | Solid tumours |
| | PF-05082566 | Lymphoma |
| KIR | IPH2101 | Myeloma, AML |
| CCR4 | KW-0761 | ATL, CTCL |
| CD27 | CDX-1127 | Solid tumours and Heme |
| Ox40 | MEDI-6469 | Solid tumours |
| CD40 | CP-870, 893 | Pancreatic |

Heme, Haematologic tumors;
ATL, acute T-cell leukemia;
CTCL, cutaneous T-cell lymphoma;
AML, acute myeloid leukemia

TABLE 2

Agents targeting PD-1/PD-L1 in clinical development

| Agent targeting PD-1 | Agent targeting PD-L1 |
|---|---|
| BMS-936558/MDX-1106 Nivolumab (fully human IgG4 mAb) | BMS-936559/MDX-1105 (fully human IgG4 mAb) |
| CT-011 Pidilizumab (humanised IgG1 mAb) | N/A |
| N/A | MPDL3280A (IgG1 mAb, Fc modified) |
| AMP-514 | MEDI4736 (fully human mAb) |
| MK-3475Pembrolizumab (humanised IgG4 mAb) | N/A |
| N/A | MSB0010718C |
| AUNP 12 (peptide) | N/A |

PD-1, programmed death 1 receptor, PD-L1, programmed cell death ligand 1;
IgG4, immunoglobulin G4;
mAb, monoclonal antibody;
N/A, not available In the first embodiment of the invention, one immune checkpoint inhibitor is provided in the kit for the treatment of cancer. It is preferred that the immune checkpoint inhibitor is an anti-CTLA-4 antibody. It is especially preferred that the immune checkpoint inhibitor is ipilimumab. In a second embodiment of the invention, at least one immune checkpoint inhibitor is provided in the kit for the treatment of cancer. In this second embodiment, first and second checkpoint inhibitors are provided, wherein the first and second checkpoint inhibitors target different immune checkpoints. It is preferred that the first immune checkpoint inhibitor targets the CTLA-4 checkpoint and the second immune checkpoint inhibitor targets the PD-1 checkpoint.

CTLA-4 and Inhibitors of the CTLA-4 Pathway:

Cytotoxic T-lymphocyte-associated antigen (CTLA-4), also known as CD 152, is a co-inhibitory molecule that functions to regulate T-cell activation.

CTLA-4 was initially identified as a negative regulator on the surface of T-cells that was upregulated shortly after initiation of a de novo immune response or stimulation of an existing response in order to dampen the subsequent immune T-cell response and prevent auto-immunity or uncontrolled inflammation. Thus, the magnitude of the developing immune response has been closely tied to CTLA-4 action. In certain embodiments, the anti-CTLA-4 antibody is Ipilimumab or Tremelimumab, Checkpoint inhibitors function by modulating the immune system's endogenous mechanisms of T cell regulation. Ipilimumab (YERVOY, Bristol-Meyers Squibb, New York, NY) is a monoclonal antibody and is the first such checkpoint inhibitor to be approved by the US Food and Drug Administration (FDA). It has become standard treatment for metastatic melanoma (Hadi et al., N. Engl. J. Med. 363:711-23. 2010; Robert et al., N. Engl. J. Med. 364:2517-26. 2011). Ipilimumab binds and blocks inhibitory signaling mediated by the T cell surface co-inhibitory molecule cytotoxic T lymphocyte antigen 4 (CTLA-4). Because the mechanism of action is not specific to one tumor type, and because a wealth of preclinical data supports the role of tumor immune surveillance across multiple malignancies (Andre et al, Clin. Cancer Res. 19:28-33. 2013; May et al. Clin. Cancer Res. 17:5233-38. 201 1), Ipilimumab is being investigated as a treatment for patients with prostate, lung, renal, and breast cancer, among other tumor types, Ipilimumab works by activating the immune system by targeting CTLA-4. Another CTLA-4-blocking antibody, Tremelimumab, continues to be investigated in clinical trials and has also demonstrated durable responses in patients with melanoma (Kirkwood et al., Clin. Cancer Res. 16: 1042-48. 2010; Rihas et al. J. Clin. Oncol. 3 1:616-22, 2013).

PD-1 and Inhibitors of the PD-1 Pathway:

Whereas CTLA-4 serves to regulate early T cell activation, Programmed Death-1 (PD-1) signaling functions in part to regulate T cell activation in peripheral tissues. The PD-1 receptor refers to an immunoinhibitory receptor belonging to the CD28 family. PD-1 is expressed on a number of cell types including T legs, activated B cells, and natural killer (NK) cells, and is expressed predominantly on previously activated T cells in vivo, and binds to two ligands, PD-L1 and PD-L2. PD-1's endogenous ligands, PD-L1 and PD-L2, are expressed in activated immune cells as well as nonhaematopoietic cells, including tumor cells. PD-1 as used herein is meant to include human PD-1 (hPD-1), variants, isoforms, and species homologs of hPD-1, and analogs having at least one common epitope with hPD-1. The complete hPD-1 sequence can be found under GENBANK Accession No. U64863. Programmed Death Ligand-1 (PD-L1) is one of two cell surface glycoprotein ligands for PD-1 (the other being PD-L2) that results in downregulation of T cell activation and cytokine secretion upon binding to PD-1. PD-L1 as used herein includes human PD-L1 (hPD-L1), variants, isoforms, and species homologs of hPD-L1, and analogs having at least one common epitope with hPD-L1. The complete hPD-L1 sequence can be found under GENBANK Accession No. Q9NZQ7. Tumors have been demonstrated to escape immune surveillance by expressing PD-L1/L2, thereby suppressing tumor-infiltrating lymphocytes via PD-1/PD-L1,2 interactions (Dong et al. Nat. Med. 8:793-800. 2002). Inhibition of these interactions with therapeutic antibodies has been shown to enhance T cell response and stimulate antitumor activity (Freeman et al. J. Exp. Med. 192: 1027-34.2000).

As discussed above, in some embodiments, the anti-PD-1 antibody is Nivolumab (CAS Registry Number: 946414-94-4). Alternative names for Nivolumab include MDX-1 106, MDX-1 106-04, ONO-4538, BMS-936558. Nivolumab is a fully human IgG4 blocking monoclonal antibody against PD-1 (Topaliam et al., N. Engl. J. Med. 366:2443-54. 2012). Nivolumab specifically blocks PD-1, which can overcome immune resistance. The ligands for PD-1 have been identified as PD-L1 (B7-H1), which is expressed on all hemopoietic cells and many nonhaemopoietic tissues, and PD-L2 (B7-DC), whose expression is restricted primarily to dendritic cells and macrophages (Dong, H, et al. 1999. Nat. Med. 5: 1365; Freeman, G. J. et al. 2000. J. Exp. Med. 192: 1027; Latehman, Y. et al. 2001. Nat. Immunol 2:261; Tseng, S. Y. et al 2001. J. Exp. Med. 193:839). PD-L1 is overexpressed in many cancers and is often associated with poor prognosis (Okazaki T et al, Intern. Immun. 2007 19(7):813) (Thompson R H et al, Cancer Res 2006, 66(7):3381), the majority of tumor infiltrating T lymphocytes predominantly express PD-1, in contrast to T lymphocytes in normal tissues and peripheral blood T lymphocytes, indicating that up-regulation of PD-1 on tumor-reactive T cells can contribute to impaired antitumor immune responses (Blood 2009 1 14(8): 1537). Specifically, since tumor cells express PD-L1, an immunosuppressive PD-1 ligand, inhibition of the interaction between PD-1 and PD-L1 can enhance T-cell responses in vitro and mediate preclinical antitumor activity.

A number of clinical trials (Phase I, II and Ill) involving Nivolumab have been conducted or are on-going. For example, in a phase I dose escalation trial, nivolumab was safe, and objective responses were 16-31% across tumor types, with most responses being durable for >1 year (Topaliam et al., Presented at Annu. Meet. Am. Soc. Clin. Oncol., Chicago, May 31-Jun. 4, 2013). In another study, the safety and clinical activity of nivolumab (anti-PD-1, BMS-936558, Q Q-4538) in combination with ipilimumab in patients with advanced melanoma was investigated (Woichok, J Olin Oncol 31, 2013 (suppl; abstr 9012 2013 ASCO Annual Meeting).

Two anti-PD-L1 inhibitory antibodies, MPDL3280A (Genentech, South San Francisco, CA) and BMS-936559 (Bristol Meyers Squibb, New York, NY), have undergone clinical investigation. Like nivolumab and MK-3475, these antibodies are thought to function principally by blocking PD-1/PD-L1 signaling. Unlike PD-1 antibodies, PD-L1 antibodies spare potential interactions between PD-L2 and PD-1, but additionally block interactions between PD-L1 and CD80 (Park et al., 2010. Blood 3 16:1291-98). MPDL3280A has been evaluated in multiple tumor types, with safety and preliminary efficacy identified in melanoma; renal cell carcinoma; non-small cell lung carcinoma (NSCLC); and colorectal, gastric, and head/neck squamous cell carcinoma (Herbst et al. presented at Annu. Meet Am. Soc. Clin. Oncol., Chicago, May 31-Jun. 4, 2013), Similarly, BMS-936559 was shown to be safe and clinically active across multiple tumor types in a phase I trial. MEDI-4736 is another PD-L1-blocking antibody currently in clinical development (NCT01693562).

In addition to CTLA-4 and PD-1/PD-L1, numerous other immunomodulatory targets have been identified primarily, many with corresponding therapeutic antibodies that are being investigated in clinical trials. Page et al. (Annu. Rev. Med. 2014.65) details targets of antibody immune modulators in FIG. 1, incorporated by reference herein.

Additional Components

In some embodiments of the invention, there are provided additional components in the kit for the treatment of cancer.

In one embodiment, the kit further comprises a pharmaceutically acceptable adjuvant, diluent or excipient.

Exemplary adjuvants include Poly I:C (Hiltonol), CpG, liposomes, microspheres, virus-like particles (ISCOMS), Freund's incomplete adjuvant, aluminium phosphate, aluminium hydroxide, alum, bacterial toxins (for example, cholera toxin and salmonella toxin). Further exemplary adjuvants include Imiquimod or glucopyranosyl Lipid A. A particularly preferred adjuvant is GM-CSF (granulocyte macrophage colony stimulating factor). Exemplary diluents and excipients include sterilised water, physiological saline, culture fluid and phosphate buffer. Exemplary adjuvants for use in vaccines targeting the T cell arm of the immune system, as in the present invention, are detailed in Petrovsky & Aguilar Immunol Cell Biol. 2004 82(5):488-96, which is incorporated herein by reference.

The polypeptide or nucleic acid molecule as described above is, in certain embodiments, coupled to an immunogenic carrier or incorporated into a virus or bacterium. Exemplary immunogenic carriers include keyhole limpet haemocyanin, bovine serum albumin, ovalbumin, fowl immunoglobulin and peptide fragments of immunogenic toxins. In one embodiment, the nucleic acid molecule is coupled to or integrated in a carrier selected from the group consisting of dendritic cells, yeast, bacteria, viral vectors, oncolytic viruses, virus like particles, liposomes, micellar nanoparticles or gold nanoparticles.

The kit, in some embodiments, also comprises a further therapeutic ingredient. Exemplary further therapeutic ingredients include interleukin-2 (IL2), interleukin-12 (IL12), a further polypeptide of a self-antigen or tumour associated antigen (that is to say, a polypeptide of a self-antigen or tumour associated antigen aside from those discussed above) chemotherapeutics, pain killers, anti-inflammatory agents and other anti-cancer agents.

Further details of additional components of the kit may be found in Remington's Pharmaceutical Sciences and US Pharmacopoeia, 1984, Mack Publishing Company, Easton, PA, USA.

In certain embodiments, the aforementioned components of the kit are provided in the form of a composition or a pharmaceutical composition for the treatment of cancer.

In one embodiment, the vaccine (i.e. the polypeptide or nucleic acid molecule) and immune checkpoint inhibitor are injected locally from the same syringe. In this embodiment, a much lower dose of the immune checkpoint inhibitor is used compared to that used when the immune checkpoint inhibitor is administered systemically (see Fransen et al. Olin Cancer Res. 2013 19(19):5381-9; Fransen et al. Oncoimmunology. 2013 2(11):e26493). That is to say, the immune checkpoint inhibitor will be used at a dosage that is at the lower end of the range of 1 microgram/kg to 10 mg/kg. The dosage of the vaccine is unchanged compared to when it is administered separately from the immune checkpoint inhibitor.

Methods of the Invention

In use, each component of the kit, the composition or the pharmaceutical composition as explained above is administered to a patient in need of treatment. In principle, any mode of administration of the components of the kit, the composition or the pharmaceutical composition may be used.

In embodiments in which the kit, the composition or the pharmaceutical composition comprises a polypeptide, the polypeptide is endocytosed by antigen presenting cells, may be subject to antigen processing and is then presented in complex with an MHC class II molecule on the cell surface. Through interaction with T-cell receptors on the surface of T-cells, a CD4+ T-cell response is elicited. It is to be appreciated that as a result of antigen processing, the polypeptide of the kit, the composition or the pharmaceutical composition may also be presented in a complex with an MHC class I molecule on the cell surface and thereby elicit a CD8+ T cell response. In embodiments in which the kit, the composition or the pharmaceutical composition comprises a nucleic acid molecule, the nucleic acid molecule is also endocytosed and is then transcribed (if the nucleic acid molecule is DNA) and translated, and the encoded polypeptide is synthesised through endogenous cellular pathways. Subsequently, the encoded polypeptide is processed and presented on an MHC molecule in order to elicit the T-cell response, as previously described. Thus the kit, the composition or the pharmaceutical composition may be used as a vaccine in order to elicit CD4+ T-cell (as well as CD8+ T cell) immunity.

In embodiments in which the kit, the composition or the pharmaceutical composition comprise a T-cell receptor, or a T-cell displaying the T-cell receptor, the T-cell or the T-cell receptor directly provides CD4+ T-cell (or CD8+ T-cell) immunity.

The components of the kit as explained above may be administered simultaneously, separately or sequentially to a patient in need of treatment. That is to say, the components of the kit may be administered at a different time, as well as in a substantially simultaneous manner. The term simultaneously as used herein refers to administration of one or more agents at the same time. For example, in certain embodiments, the at least one polypeptide of a self-antigen and the immune checkpoint inhibitor are administered simultaneously. Simultaneously includes administration contemporaneously, that is during the same period of time. In certain embodiments, the one or more agents are administered simultaneously in the same hour, or simultaneously in the same day. In some embodiments, the term "sequentially" refers to the components of the kit being administered within 1, 3, 5, 7, 10, 30 or 60 days of each other. In some embodiments, the term "sequentially" refers to the components of the kit being administered within 2, 4 or 6 months of each other, As explained above, the second component of the kit (i.e. the immune checkpoint inhibitor) is capable of down-regulating or blocking an immune checkpoint to allow more extensive immune activity. In some embodiments, it is preferred to administer the second component of the kit subsequent to the first component of the kit. In this way, the second component of the kit takes effect as a T-cell immune response is initiated in response to vaccination with the first component of the kit (which, in some embodiments, is the at least one polypeptide or the nucleic acid molecule). It is preferred to administer the second component of the kit during the initiation phase of vaccination. In some embodiments, this is within 30, 21, 14, 10, 7, 5, 3 or 1 days from the initial vaccination with the first component of the kit. Further details on treatment regimes in accordance with embodiments of the present invention are described below.

Without wishing to be bound by theory, it is thought that the administration of the second component of the kit subsequent to the first component of the kit and within the aforementioned timeframe promotes a rapid and effective expansion of T-cells specific to the first component of the kit from a population of naïve T-cells in the primary lymphoid organs (i.e. a rapid and effective primary immune response). This is thought to be because the second component of the kit takes effect as the T-cell response is developing and prevents dampening of the response by the immune checkpoint. Therefore, a strong de novo immune response is promoted, which translates into higher clinical benefit as described below. In addition, the administration of the second component of the kit subsequent to the first component of the kit and within the aforementioned timeframe is thought to contribute to the generation of an accelerated CD4+ T cell immune response.

Sequential or substantially simultaneous administration of each component of the kit can be effected by any appropriate route including, but not limited to, intradermal routes, oral routes, intravenous routes, sub-cutaneous routes, intramuscular routes, direct absorption through mucous membrane tissues (e.g., nasal, mouth, vaginal, and rectal), and ocular routes (e.g., intravitreal, intraocular, etc.). The components of the kit can be administered by the same route or by different routes. In is particularly preferred that the components of the kit are administered by injection. In one embodiment, the components of the kit are injected directly into a tumour in a patient. If the cancer to be treated is in the nose or mouth of a patient then in some embodiments, the components of the kit, the composition or the pharmaceutical composition are administered by spray and inhalation.

A suitable dosage of the first component of the kit (which, in some embodiments, is the at least one polypeptide of the self-antigen or a nucleic acid molecule encoding the at least one polypeptide) is between 100 and 700 μg although dosages outside this range may occasionally be required (e.g. from 1-1500 μg). A dosage of 300 μg is particularly preferred. In one embodiment, the first component of the kit is a T-cell and a dose of $10^6$ to $10^{11}$ cells is provided. A suitable dosage of the second component of the kit (i.e. the immune checkpoint inhibitor) is 3 mg/kg although other dosages may occasionally be required (e.g. from 1 microgram/kg to 10 mg/kg), In some embodiments, a treatment regimen is pursued which comprises between two and five administrations of the second component of the kit (i.e. the immune checkpoint inhibitor) wherein each administration is separated by between two and five weeks. In a preferred embodiment, a treatment regimen is pursued which comprises three administrations of the immune checkpoint inhibitor) wherein each administration is separated by three weeks.

In some embodiments, the first component of the kit (which, in some embodiments, is the at least one polypeptide, the nucleic acid molecule or the T-cell receptor or T-cell displaying the T cell receptor) is administered to the patient according to the following treatment regimen. The first component of the kit is administered: (i) prior to the first administration of the immune checkpoint inhibitor; (ii) prior to each re-administration of the immune checkpoint inhibitor; and (iii) following completion of the immune checkpoint inhibitor treatment regimen. It is preferred that multiple administrations of the first component of the kit are provided at stages (i), (ii) and (iii).

It is particularly preferred that one to five administrations of the first component of the kit are provided at stages (i) and (ii) in the seven days prior to the first administration or re-administration of the checkpoint inhibitor respectively. It is especially preferred that one to three administrations of the first component of the kit are provided. In some embodiments, the administration of the first component of the kit at stage (i) is provided between one to three days prior to the first administration of the checkpoint inhibitor. It is also preferred that the first component of the kit is administered to the patient following completion of the immune checkpoint inhibitor treatment regimen on a monthly basis (i.e. stage (iii)). In an alternative embodiment, the administration of the first component of the kit at stage (iii) is on a quarterly basis.

In one embodiment, the first component of the kit is administered with an additional component as explained above. It is particularly preferred that the first component of the kit is administered with GM-CSF. A suitable dosage of GM-CSF is between 50 and 100 μg. A dosage of 75 μg is particularly preferred.

In some embodiments, the treatment regimen using the first and second components of the kit lasts for a total of 48 weeks from the first administration of the second component of the kit. In alternative embodiments, the treatment regimen is shorter or longer than 48 weeks.

As previously stated, the at least one polypeptide is of a self-antigen and/or a universal tumour antigen, which are associated with a wide range of cancer types. Therefore, the efficacy of the present invention is not limited to any particular type of cancer. In one embodiment, the self-antigen and/or a universal tumour antigen is hTERT and so in principle, the components of the kit, the composition or the pharmaceutical composition may be administered to a patient suffering from any type of cancer in which the telomerase gene is activated. Such cancers include but are not limited to breast cancer, prostate cancer, pancreatic cancer, colorectal cancer, lung cancer, bladder cancer, malignant melanoma, leukaemias, lymphomas, ovarian cancer, cervical cancer and biliary tract carcinomas. However, as the telomerase enzyme is expressed in the vast majority of cancers, it is to be understood the efficacy of the invention is not limited to any particular type of cancer.

That telomerase is expressed in the vast majority of cancers has been demonstrated in studies such as Kim et al. Science. 1994 Dec. 23; 266(5193):2011-5 and Bearss et al. Oncogene. 2000 Dec. 27; 19(56):6632-41 (both are incorporated herein by reference).

Kim et al. 1994 has demonstrated that, in cultured cells representing 18 different human tissues, 98 of 100 immortal and none of 22 mortal populations were positive for telomerase. The human tissues from which the immoral cell lines having telomerase activity were derived included: skin, connective, adipose, breast, lung, stomach, pancreas, ovary, cervix, kidney, bladder, colon, prostate, CNS, retina and blood. The present invention would therefore be suitable for use against cancers derived from these tissues. Similarly, 90 of 101 biopsies representing 12 human tumour types and none of 50 normal somatic tissues were positive for telomerase. The human tumour types which exhibited telomerase activity included: hepatocellular carcinoma, colon cancer, squamous cell carcinoma (head and neck), Wilms tumor, breast cancer (ductal and lobular, node positive), breast cancer (axillary node negative), prostate cancer, prostatic intraepithelial neoplasia type 3, benign prostatic hyperplasia, neuroblastoma, brain tumors, lung small-cell carcinoma, rhabdomyosarcoma, leiomyosarcoma, hematological malignancies (including acute lymphocytic leukaemia, chronic lymphocytic leukaemia, lymphoma (adult)).

Bearss et al. 2000 has furthermore demonstrated the presence of telomerase activity in tumour cells taken directly from patients across a wide range of cancer types. These tumour types included: hematologic malignancies (including acute myeloid leukaemia, acute lymphoid leukaemia, chronic myeloid leukaemia, chronic lymphoid leukaemia (early), chronic lymphoid leukaemia (late); myeloma, low-grade lymphoma, high-grade lymphoma); breast; prostate; lung (including non-small cell and small cell); colon; ovarian; head and neck; kidney; melanoma; neuroblastoma; glioblastoma; hepatocellular carcinoma; gastric; and bladder.

It is to be understood that, as telomerase is activated in the above-mentioned cancer types, the present invention is suitable for use against any one of these types of cancer (and indeed any cancer type in which telomerase is activated). Furthermore, it is apparent that, as the activation of telomerase is a common property shared between cancer types, the present invention is not limited to any particular type of cancer.

It is to be noted that some of the polypeptides of the present invention (e.g. the polypeptide of SEQ. ID NO. 1) are longer than would normally be accommodated in either an MHC class I or class II molecule. Peptides of this length have been shown to induce more robust immune responses, e.g by groups working on HPV and cervical cancer vaccination (Welters et al, 2008). Without wishing to be bound by theory, it is believed that such polypeptides, following their administration to a patient, are endocytosed by cells, subjected to proteolytic degradation in the proteasome and then presented on an MHC class I or class II molecule. Thus such polypeptides may give rise to an MHC class and/or an MHC class II restricted T-cell response. It is to be appreciated that this is demonstrated by FIG. 6 (see Example 6) because different CD4+ cell clones reactive with SEQ. ID NO. 1 recognise different peptide fragments from this 30-mer polypeptide as a result of proteolytic cleavage. It is also to be appreciated that longer polypeptides remain extant within a patient for a greater period of time than shorter polypeptides and therefore there is a longer period of time during which they may elicit an immune response. This is particularly significant as regards those polypeptides which have a relatively low MHC binding affinity.

It is also to be appreciated that individuals will generally have developed some degree of immunological tolerance to polypeptides of self-antigens through a process whereby T-cells reactive with such polypeptides are destroyed in the thymus of the individual during T-cell development. Thus in some embodiments of the present invention, polypeptides of the present invention with a relatively low MHC binding affinity are desired. This is because polypeptides with lower MHC binding affinity will have been exposed to maturing T-cells at a lower rate and so it is less likely that all of the individual's T-cells reactive with the polypeptide will have been deleted from the individual's T-cell repertoire. Thus polypeptides having a relatively low MHC binding affinity are, in some embodiments, able to overcome immunological tolerance more readily.

Synergistic Effect

The at least one polypeptide of a self-antigen or universal tumour antigen, which is at least 12 amino acids in length and the checkpoint inhibitor produce a synergistic effect in the treatment of cancer. In other embodiments, the nucleic acid molecule, the T-cell receptor, or the T-cell displaying the T-cell receptor, according to the present invention and the immune checkpoint inhibitor produce a synergistic effect in the treatment of cancer.

The synergistic effect in the treatment of cancer comprises: a reduction in the time required by the immune system of the patient to mount a measurable immune response against the at least one polypeptide of a self-antigen or universal tumour antigen; the mounting of a strong immune response to the at least one polypeptide (i.e. a Stimulation Index, SI≥3); and an improved clinical outcome (i.e. a partial or complete response (also known as partial or complete remission) or stable disease). In some embodiments, the synergistic effect in the treatment of cancer also comprises the induction of a broad immune response (i.e. the mounting of an immune response against 2, 3 or more vaccine components).

Without wishing to be bound by theory, it is believed that the ability of the at least one polypeptide of the self-antigen to elicit a CD4+ T cell response is of central importance to the synergistic effect. Referring to FIG. 1, the mechanism by which the polypeptide of the present invention is expected to elicit a CD4+ T cell response is shown. By using long polypeptides, CD4+ T cells are stimulated. These cells play a complex role in the tumour microenvironment and are able to interact directly with tumour cells and a number of immune effectors, leading to tumour cell destruction. Dead tumour cells release more antigen which in turn is taken up by antigen presenting cells, stimulating a second wave of T-cell immunity targeting other tumour antigens, a phenomenon called "epitope spreading".

The combination of the polypeptide capable of eliciting a CD4+ T cell response and the immune checkpoint inhibition results in a fast occurring immune response in a high proportion of patients as well as efficient augmentation of low/non-detectable immune responses in other patients. This results in a high clinical response rate (i.e. the proportion of patients with a partial or complete response (also known as partial or complete remission) or stable disease. In particular, the polypeptide of the self-antigen and/or universal tumour antigen provides a cancer-specific immune response to patients lacking such a response, and will also augment weak or suboptimal spontaneous immune response in the patients thus greatly extending the number of patients that may benefit clinically from immune checkpoint inhibition. The immune checkpoint inhibition removes the negative influence of the checkpoint on T cell proliferation and thus results in a more rapid and clinically efficient T cell response in a higher proportion of patients. This includes turning negative responses to the polypeptide of the self-antigen and/or tumour associated antigen into a positive response by allowing extended clonal expansion long after termination of vaccination with the polypeptide.

It is to be appreciated that the present invention is particularly useful in the following clinical settings. First, in patient groups in which the patient has a tumour where spontaneous immune responses are generally absent (i.e. tumour indications where immune checkpoint inhibition has previously failed to provide clinical benefit) and in patients groups where only a small fraction of patients are responsive to immune checkpoint inhibition (e.g. patients with malignant melanoma). Second, in patient groups where previous cancer vaccines have demonstrated their capacity to elicit immune responses to long peptide vaccines and patients where cancer vaccines can be developed, but are unable to provide substantial clinical benefit despite their capacity to induce immune responses after vaccination. In one embodiment, the present invention is used in patient groups where immune checkpoint therapy currently has marginal or no clinical benefit and the invention elicits de novo immune responses following vaccination with the at least one polypeptide of a self-antigen.

EXAMPLES

Hereinafter, the invention will be specifically described with reference to the Examples. However, these Examples do not limit the technical scope of the invention.

Materials and Methods

T Cell Response Assay (Proliferation by 3H-Thymidine Incorporation)

Peripheral blood mononuclear cells (PBMCs) were obtained prior to the start of vaccination and at multiple time points after vaccination. The PBMCs were isolated and frozen as previously described (Inderberg-Suso E M et al., Oncoimmunology 2012 1(5):670-686, which is incorporated herein by reference). T cell cultures generated from pre- and post-vaccination PBMCs, after one in vitro pre-stimulation with the vaccine peptide were subsequently tested in a standardised T cell proliferation assay using 3H-Thymidine incorporation as previously described (Inderberg-Suso E M et al., Oncoimmunology 2012 1(5):670-686). Irradiated autologous PBMCs were used as antigen presenting cells (APCs). T cells (50000) were incubated with 50000 APCs with and without the relevant antigen (e.g. the combination of SEQ ID NOS. 1, 2 and 3 as well as the individual polypeptides of SEQ ID NOS. 1, 2 and 3). T cell cultures were tested in triplicates. The standard error of the mean (SEM) was usually below 10%. T cell bulk responses were considered antigen-specific when the stimulatory index (SI; response with antigen divided by response without antigen) was equal to or above 3 (SI≥3).

ELISPOT Assay

The IFN-γ ELISPOT assays were performed essentially as previously described (Gjertsen M K et al, J Mol Med (Berl) 2003; 81:43-50). Monoclonal antibody against human IFN-γ (Mabtech) was diluted with PBS to a final concentration of 5 μg/ml, 96-well MultiScreen-HA plates (Millipore) were coated with antibody by adding 75 μl/well of the stock solution and incubated overnight at 4° C. The following day, plates were stored at room temperature for 1 h before washing wells six times with PBS 200 to remove excess antibody. To block unspecific binding, plates were incubated for 1-2 h at 37° C. with 100 μl per well of CellGro DC medium plus 10% human serum (HS; Baxter) Thawed and washed autologous PBMCs were enumerated and added to the pre-coated wells at 5×105 cells/well. The responder T cells were harvested, washed, enumerated and transferred in CellGro DC medium (CellGenix) in triplicates to the wells containing autologous PBMCs at 1×10$^5$ cells per well. Negative controls with T cells only and PBMCs only and positive controls with T cells+PBMC+*Staphylococcus enterotoxin* C3 (SECS; Toxin Technologies) were included. After overnight incubation at 37° C. with 5% CO2 in a humidified incubator, the plates were washed six times with PBS. Between the second and third wash, the plates were incubated for 10 min at room temperature. To each well, 75 μl of a stock solution of 1 μg/ml of biotinylated antibody against human IFN-γ (Mabtech) was added and plates were incubated for 2 h at room temperature. Following six repeated washings, plates were incubated for 1 h with 75 μl per well of streptavidin-ALP (Mabtech) from a stock solution (diluted 1:1000 in PBS plus 1% HSA). To remove excess antibody, the wells were again washed six times with PBS. Then, after adding 75 μl of substrate BCIP/NBT (Sigma-Aldrich) to each well, plates were incubated for 5-20 min. When spots appeared, water was added to stop the reaction. Spots were enumerated using an automated analyzer, CTL IMMUNOSPOT S5 VERSA-02-9030 (Cellular Technology Ltd).

Example 1: Polypeptides Having the Sequences of SEQ. ID NOS. 1 and 2 and a Combination of SEQ ID NOS. 1, 2 and 3 are Capable of Eliciting a CD4+ T Cell Response Peripheral blood T cell responses in a melanoma patient who had been vaccinated with SEQ ID NOS: 1, 2 and 3. The T cells were stimulated in vitro with SEQ. ID NOS. 1, 2 or 3 as well as a combination of all three polypeptides. T cell proliferation assays and ELISPOT assays were performed as per the Materials and Methods section as set out herein. The results are presented in FIGS. 2A and 2B and in Tables 3A to 3C below. 719-20 refers to SEQ. ID NO: 1, 725 refers to SEQ. ID NO. 2, 728 refers to SEQ. ID NO. 3, and hTERT1 mix refers to a combination of SEQ. ID NOS. 1, 2 and 3. A stimulation index (SI) was calculated for all polypeptides tested in the T cell proliferation assay. SI≥3 was considered positive.

TABLE 3A

Results of T cell proliferation assay

| | #02 ES | | | |
|---|---|---|---|---|
| | Week −1 | Week 4 | Week 7 | Week 12 |
| 719-20 | 0.9 | 22.1 | 56.3 | 17.7 |
| 725 | 1.0 | 13.7 | 16.8 | 15.3 |
| 728 | 0.9 | 0.7 | 0.5 | 0.8 |
| hTert 1 mix | 0.9 | 25.2 | 60.0 | 20.1 |

TABLE 3B

Results of ELISPOT assay

| | T | APC | T + APC | Sec 3 | 719-20 | 725 | 728 | hTert 1 mix |
|---|---|---|---|---|---|---|---|---|
| Average spot conts | 0 | 0 | 1 | 115 | 182 | 196 | 1 | 163 |
| Standard deviation | 0.6 | 0 | 1 | 24 | 57 | 107 | 1 | 96 |

TABLE 3C

Summary of data

| Sample time point | Immune response Proliferation | Immune response ELISPOT |
|---|---|---|
| Visit 1 week −1 | No | Not done |
| Visit 8 week 4 | Yes | Not done |
| Visit 10 week 7 | Yes | Not done |
| Visit 13 week 12 | Yes | Yes |

Figure 2A:
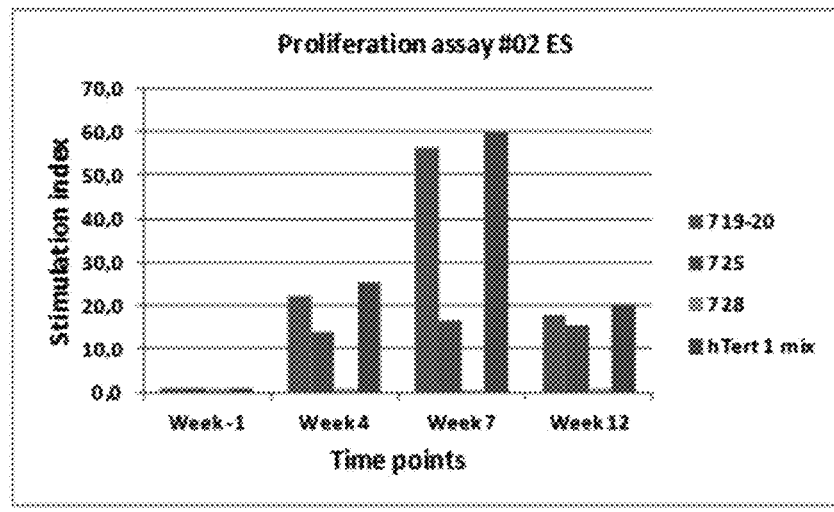
FIGS. 2A and 2B are bar graphs summarising T-cell responses detected in a melanoma patient vaccinated with a combination of SEQ. ID NOS. 1, 2 and 3 using a T cell proliferation assay and an ELISPOT assay respectively. CD4+ T-cell responses against SEQ. ID NOS. 1 and 2 as well as the combination of SEQ ID NOS. 1, 2 and 3 were detected. Proliferation in response to peptide-loaded PBMC was measured by 3H-thymidine incorporation. A stimulation index of ≥3 is considered an immune response. 719-20 refers to SEQ. ID NO: 1, 725 refers to SEQ. ID NO. 2, 728 refers to SEQ. ID NO. 3, and hTERT1 mix refers to a combination of SEQ. ID NOS. 1, 2 and 3.
Figure 2B:
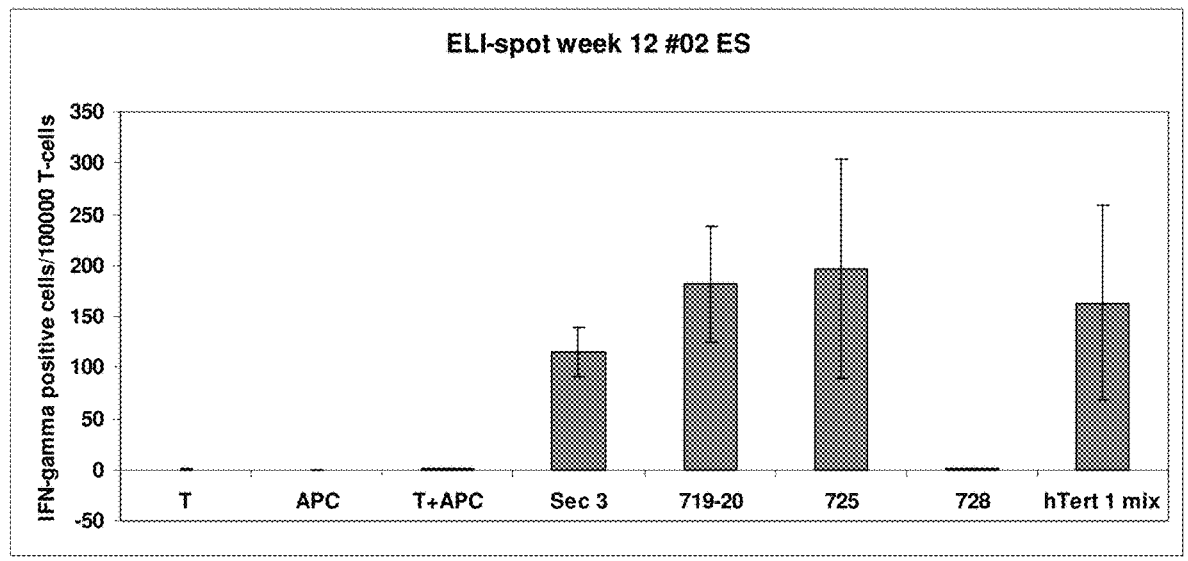

Referring to FIGS. 2A, it is shown that SEQ ID NOS: 1, 2 and the combination of SEQ ID NOS: 1, 2 and 3 elicited a strong immune response in the melanoma patient at weeks 4, 7 and 12 following vaccination with a combination of SEQ ID NOS: 1, 2 and 3. This assay is the standard assay for CD4+ T cell responses. Referring to FIG. 2B, it is shown that a positive immune response to SEQ ID NOS. 1, 2 and the combination of SEQ. ID NOS. 1, 2 and 3 was detected using the ELISPOT assay at week 12 following vaccination in the melanoma patient. This assay has mainly been developed for measuring CD8+ T cell responses, Therefore, SEQ. ID NOS. 1, 2 and the combination of SEQ. ID NOS. 1, 2 and 3 were capable of eliciting a CD4+ T cell response in a melanoma patient.

Example 2: Immunogenicity of Polypeptide Fragments of a Polypeptide Having a Sequence of SEQ ID NO. 1

CD4+ T-cells were generated from two melanoma patients (patients P7 and P9) and a lung cancer patient (patient P5). The patients had not previously been administered a cancer vaccine. The CD4+ T cells were stimulated in vitro with SEQ. ID NO. 1 or fragments thereof comprising 14 amino acids (as set out in Table 4 below). A T cell proliferation assay was performed as per the Materials and Methods section as set out herein, SI≥2 was considered positive. The results are presented in FIGS. 3A-C.

TABLE 4

Polypeptide fragments of a polypeptide having a sequence of SEQ ID No. 1

| SEQ ID NO. | SEQUENCE | FRAGMENT NAME |
|---|---|---|
| 1 | ALFSVLNYERARRPGLLGASVLGLDDIHRA | 719-20 |
| 7 | ALFSVLNYERARRP | 719-20-1 |
| 8 | LFSVLNYERARRPG | 719-20-2 |
| 9 | FSVLNYERARRPGL | 719-20-3 |
| 10 | SVLNYERARRPGLL | 719-20-4 |
| 11 | VLNYERARRPGLLG | 719-20-5 |
| 12 | LNYERARRPGLLGA | 719-20-6 |
| 13 | NYERARRPGLLGAS | 719-20-7 |
| 14 | YERARRPGLLGASV | 719-20-8 |
| 15 | ERARRPGLLGASVL | 719-20-9 |
| 16 | RARRPGLLGASVLG | 719-20-10 |
| 17 | ARRPGLLGASVLGL | 719-20-11 |
| 18 | RRPGLLGASVLGLD | 719-20-12 |
| 19 | RPGLLGASVLGLDD | 719-20-13 |
| 20 | PGLLGASVLGLDDI | 719-20-14 |
| 21 | GLLGASVLGLDDIH | 719-20-15 |
| 22 | LLGASVLGLDDIHR | 719-20-16 |
| 23 | LGASVLGLDDIHRA | 719-20-17 |

Figure 3A:
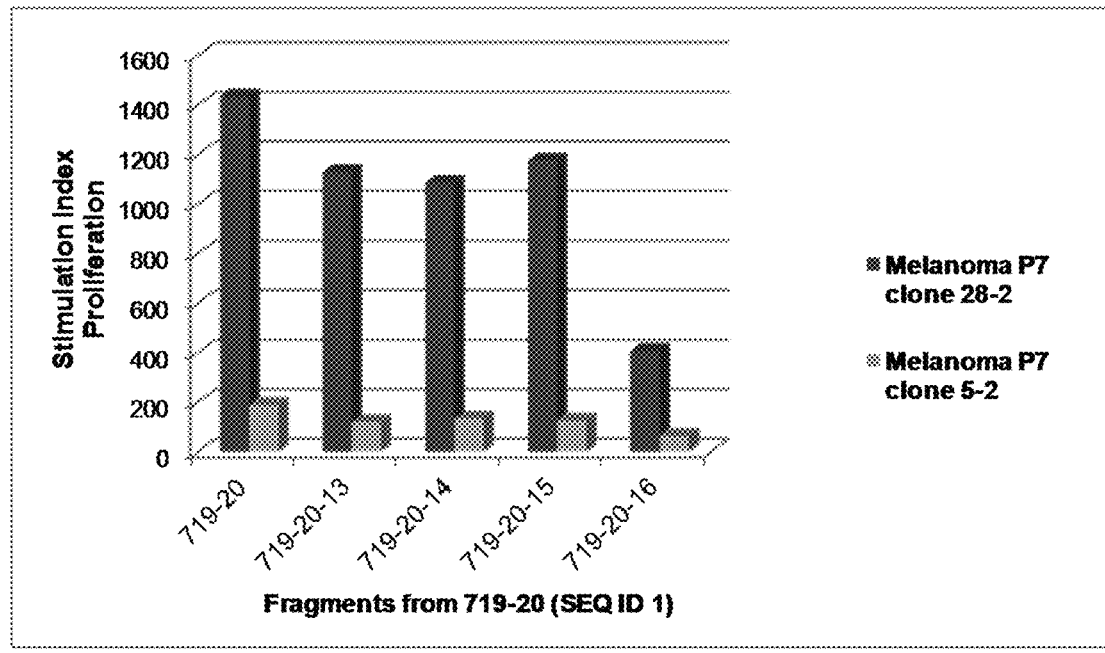
FIGS. 3A-C are bar graphs summarising CD4+ T-cell responses detected in melanoma patients and a lung cancer patient against polypeptides having a sequence of SEQ ID NO. 1 and fragments thereof. Proliferation in response to peptide-loaded PBMC was measured by 3H-thymidine incorporation. A stimulation index of ≥2 is considered an immune response. 719-20-13 to 719-20-16 and 719-20-2 to 719-20-9 refer to fragments of SEQ ID NO. 1 comprising 14 amino acids thereof.

Referring to FIG. 3A, the stimulation of T cell clones (clones 28-2 and 5-2) taken from melanoma patient P7 by a peptide having a sequence of SEQ ID No. 1 and by the peptide fragments, 719-20-13, 719-20-14, 719-20-15, and 719-20-16 is shown. Each peptide elicited a strong response from clones 28-2 and 5-2. The SI of clone 28-2 was exceptionally high and demonstrates that these peptides can select T cell clones of unusually high activity from the T cell repertoire of cancer patients. Since both clones were HLA-DQ6 restricted, these results further demonstrate that the repertoire of T cells recognising these peptides presented by a given HLA class-II molecule is complex.

Figure 3B:
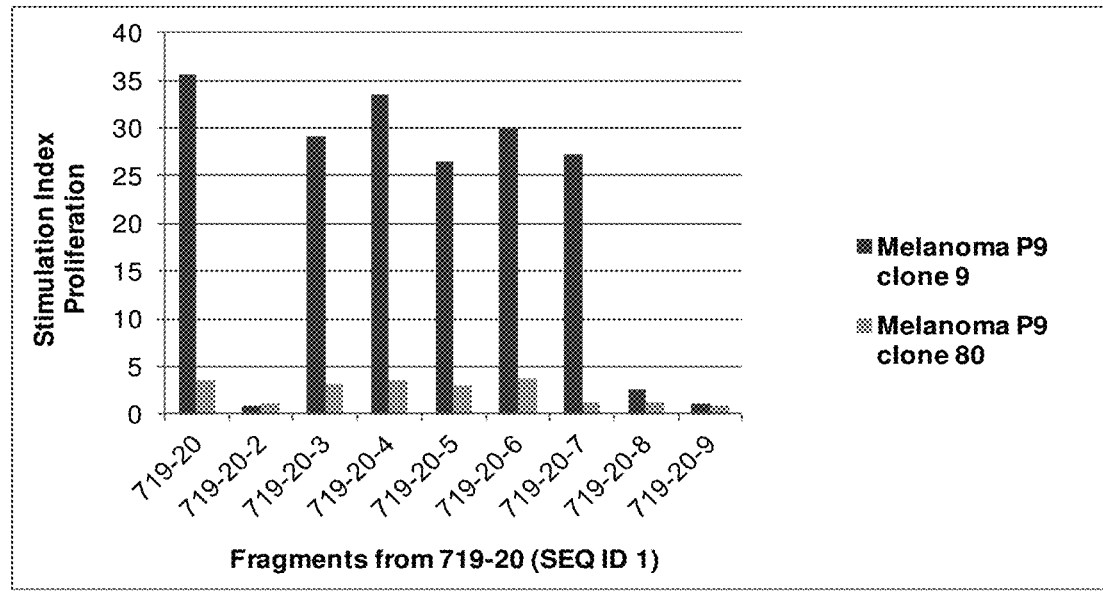

Referring to FIG. 3B, the stimulation of T cell clones (clone 9 and 80) taken from melanoma patient P9 by a peptide having a sequence of SEQ ID No. 1 and by the peptide fragments 719-20-2, 719-20-3, 719-20-4, 719-20-5, 719-20-6, 719-20-7, 719-20-8, and 719-20-9 is shown. Particularly strong stimulation of the T cell clone 9 of melanoma P9 was seen for peptide fragments 719-20, 719-20-3, 719-20-4, 719-20-5, 719-20-6 and 719-20-7, Both of these T cell clones were HLA-DR8 restricted, demonstrating again that T cells recognising the same peptide presented by the same HLA class-II molecule are heterogeneous.

Figure 3C:
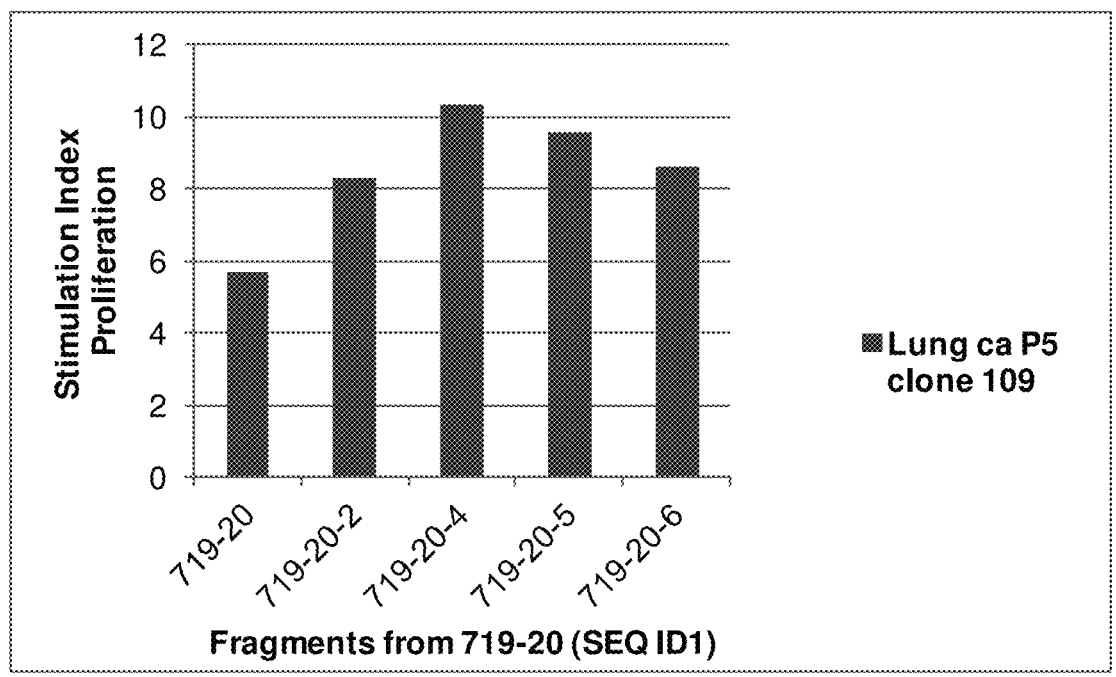

Referring to FIG. 3C, the stimulation of a T cell clone (clone 109; HLA-DR8 restricted) taken from a lung cancer patient P5 by a peptide having a sequence of SEQ ID No. 1 and by the peptide fragments 719-20-2, 719-20-4, 719-20-5, and 719-20-6 is shown. Each peptide elicited a strong response from clone 109.

In conclusion, the peptide fragments of SEQ ID NO. 1 successfully stimulated CD4+ T cell clones from patient samples. Furthermore, 12/17 peptide fragments tested were recognised between the five T cell clones tested.

Example 3: MHC Class II Binding Motifs of SEQ ID NO. 1

MHC class II binding motifs of SEQ ID NO. 1 and the immunogenic fragments of the sequence were calculated and are shown in Table 5.

TABLE 5

MHC class II binding motifs of SEQ ID NO. 1 and immunogenic fragments thereof

| SEQ ID NO. | Sequence | MHC Binding Motif |
|---|---|---|
| 1 | ALFSVLNYERARRPGLLGASVLGLDDIHRA | Th (HLA-DR*01, 04, 07, 15) |
| 24 | SVLNYERARRPGLLG | Th (HLA-DR*01, 04, 07, 15) |

TABLE 5-continued

MHC class II binding motifs of SEQ ID NO. 1 and immunogenic fragments thereof

| SEQ ID NO. | Sequence | MHC Binding Motif |
|---|---|---|
| 25 | FSVLNYERARRPGLL | Th (HLA-DR*01, 04, 07, 15) |
| 26 | ARRPGLLGASVLGLD | Th (HLA-DR*01, 04, 07, 15) |
| 27 | RARRPGLLGASVLGL | Th (HLA-DR*01, 04, 07, 15) |
| 28 | VLNYERARRPGLLGA | Th (HLA-DR*01, 04, 07, 15) |
| 29 | RPGLLGASVLGLDDI | Th (HLA-DR*01, 04, 07, 15) |
| 30 | VLNYERARRPGLLGA | Th (HLA-DR*01, 04, 07, 15) |

As can be seen from Table 5, the polypeptide of SEQ. ID NO: 1 and its immunogenic fragments are able to bind to a wide range of HLA molecules (note that only those presenting Th epitopes are shown in Table 5). Therefore, this polypeptide is able to generate immune responses over a very broad patient population.

Example 4: Immunogenicity of Polypeptide Fragments of a Polypeptide Having a Sequence of SEQ ID NO. 2

CD4+ T-cells were generated from a melanoma patient (patient P7) and an ovarian cancer patient (patient P1). The patients had not previously been administered a cancer vaccine. The CD4+ T cells were stimulated in vitro with SEQ. ID NO. 2 or fragments thereof comprising 12 amino acids (as set out in Table 6 below). A T cell proliferation assay was performed as per the Materials and Methods section as set out herein. SI 2 was considered positive. The results are presented in FIG. 4.

TABLE 6

Polypeptide fragments of a polypeptide having a sequence of SEQ ID No. 2

| SEQ ID NO. | SEQUENCE | FRAGMENT NAME |
|---|---|---|
| 2 | RTFVLRVRAQDPPPE | 725 |
| 31 | RTFVLRVRAQDP | 725-1 |
| 32 | TFVLRVRAQDPP | 725-2 |
| 33 | FVLRVRAQDPPP | 725-3 |
| 34 | VLRVRAQDPPPE | 725-4 |

Figure 4:
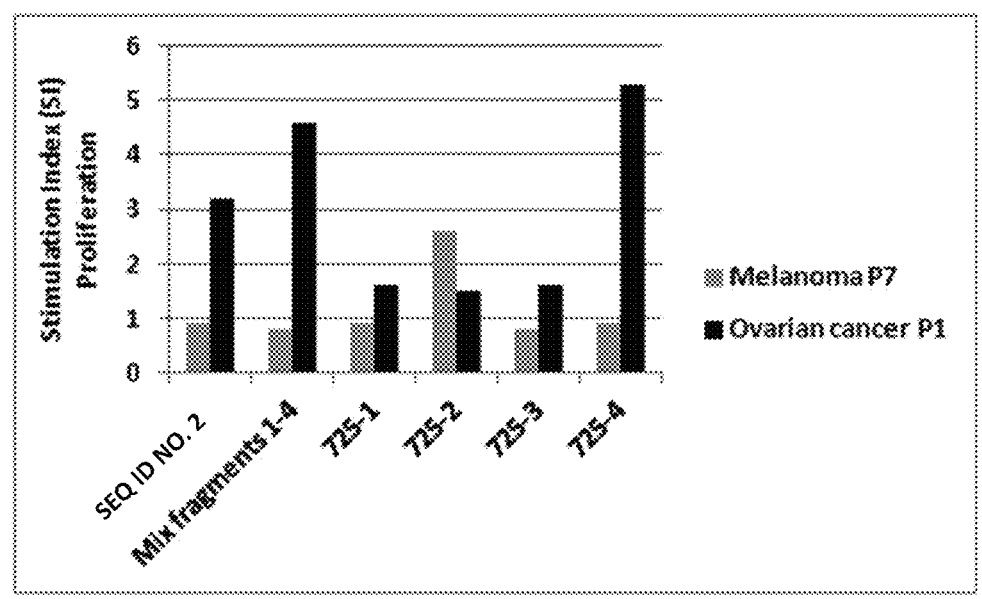
FIG. 4 is a bar graph summarising CD4+ T-cell responses detected in a melanoma patient and an ovarian cancer patient against polypeptides having a sequence of SEQ ID NO. 2 and fragments thereof. Proliferation in response to peptide-loaded PBMC was measured by 3H-thymidine incorporation. A stimulation index of ≥2 is considered an immune response. 725-1 to 725-4 refer to fragments of SEQ ID NO. 2 comprising 12 amino acids thereof.

Referring to FIG. 4, the stimulation of T cells taken from melanoma patient P7 and from ovarian cancer P1 by a polypeptide having a sequence of SEQ ID No. 2 and by the polypeptide fragments, 725-2 and 725-4 is shown.

The polypeptide fragments of SEQ ID NO. 2 successfully stimulated the T cells from patient samples. Furthermore, 2/4 polypeptide fragments tested were recognised between the cancer patients tested.

Example 5: A Polypeptide Having the Sequence of SEQ. ID NO. 3 and Fragments Thereof are Capable of Eliciting a CD4+ T Cell Response CD4+ T cells were generated from one patient with pancreatic cancer (patient P1) and one patient with glioblastoma (patient P5) who had not been administered a cancer vaccine. The CD4+ T cells were stimulated in vitro with SEQ. ID NO. 3 or fragments thereof comprising 12 amino acids (as set out in Table 7 below). A T cell proliferation assay was performed as per the Materials and Methods section as set out herein. SI 3 was considered positive. The results are presented in FIG. 5.

TABLE 7

Polypeptide fragments of a polypeptide having a sequence of SEQ ID No. 3

| SEQ ID NO. | SEQUENCE | FRAGMENT NAME |
|---|---|---|
| 3 | AERLTSRVKALFSVL | 728 |
| 35 | AERLTSRVKALF | 728-1 |
| 36 | ERLTSRVKALFS | 728-2 |
| 37 | RLTSRVKALFSV | 728-3 |
| 38 | LTSRVKALFSVL | 728-4 |

Figure 5:
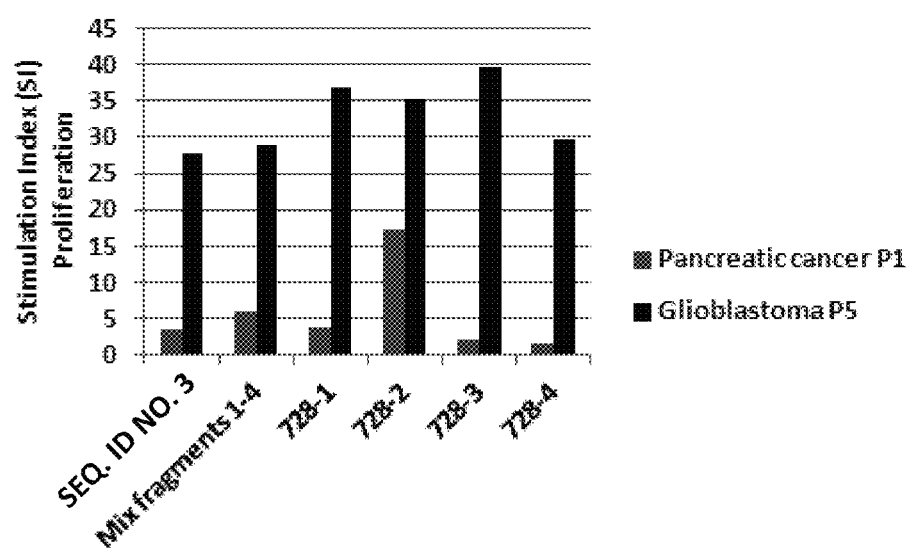
FIG. 5 is a bar graph summarising CD4+ T-cell responses detected in a pancreatic cancer patient and a glioblastoma patient against polypeptides having a sequence of SEQ ID No. 3 and fragments thereof. Proliferation in response to peptide-loaded PBMC was measured by 3H-thymidine incorporation. A stimulation index of ≥3 is considered an immune response. 728-1 to 728-4 refer to fragments of SEQ ID NO. 3 comprising 12 amino acids thereof.

Referring to FIG. 5, it is shown that a polypeptide having a sequence of SEQ ID NO. 3 and fragments thereof elicited a CD4+ T cell response in a non-vaccinated pancreatic cancer and a glioblastoma patient. Particularly strong stimulation of the CD4+ T cells was seen for peptide fragment 728-2 in the pancreatic cancer patient whereas all fragments strongly stimulated cells from the glioblastoma patient.

In conclusion, SEQ ID NO. 3 and fragments thereof were capable of stimulating CD4+ T cells in non-vaccinated pancreatic cancer and glioblastoma cancer patients.

Example 6: Polypeptide Fragments of a Polypeptide Having the Sequence of SEQ. ID NO. 1 are Capable of Eliciting a CD4+ T Cell Response CD4+ T cell clones specific for SEQ. ID NO. 1 were generated from a patient that had been vaccinated with the combination of SEQ. ID NOS. 1, 2 and 3 and were stimulated with an overlapping library of 14-mer peptides of SEQ. ID NO. 1. T cell clone proliferation was measured after peptide stimulation using a T cell response assays (proliferation by 3H-Thymidine incorporation) as per the Materials and Methods. The data are shown in FIG. 6.

Figure 6:
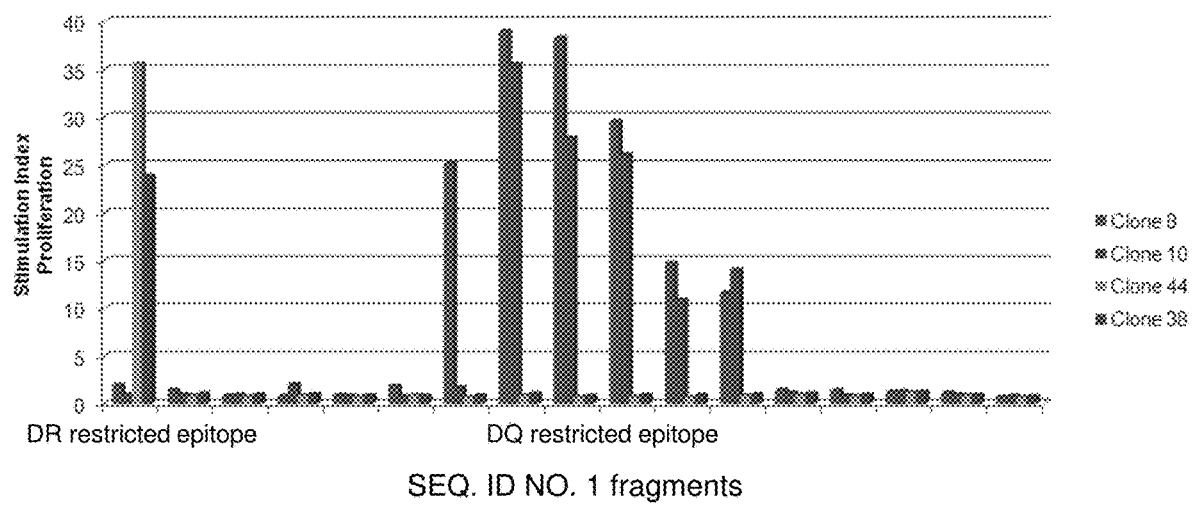
FIG. 6 is a bar graph summarising CD4+ T-cell responses detected in a cancer patient with prostate cancer vaccinated with a combination of SEQ. ID NOS. 1, 2 and 3. CD4+ T-cell responses against overlapping 14-mer peptides from SEQ. ID NO. 1 were detected following vaccination and responding T cells cloned. The data in FIG. 6 indicate proliferative responses of selected CD4+ T cell clones. Proliferation in response to peptide-loaded PBMC was measured by 3H-thymidine incorporation. A stimulation index of is considered an immune response.

Referring to FIG. 6, it is shown that CD4+ T cell clones specific for SEQ. ID NO. 1 recognised different 14-mer fragments of the SEQ. ID NO. 1 polypeptide depending on HLA restriction. Therefore, vaccination with the full-length SEQ. ID NO. 1 is capable of producing a broad CD4+ T cell response because T cell clones of different HLA restriction are stimulated (e.g. HLA-DR and HLA-DQ restricted T cell clones).

In conclusion, fragments of a polypeptide having the sequence of SEQ ID NO. 1 were capable of eliciting a CD4+ T cell response in T cell clones of different HLA restrictions.

Example 7: Clinical Response Data from Patients with Unresectable or Metastatic Malignant Melanoma Who Received a Cancer Vaccine in Combination with Ipilimumab Combination treatment with an anti-CTLA-4 blocking agent and a cancer vaccine (which comprised long peptides capable of inducing a cancer specific T helper cell response) was investigated in a clinical trial. In the trial (EudraCT number: 2013-005582-39) the combination of ipilimumab and a cancer vaccine comprising a cocktail of SEQ ID NOS: 1, 2 and 3 was investigated in patients with unresectable or metastatic malignant melanoma.

Ipilimumab is a fully human monoclonal immunoglobulin specific for human cytotoxic T lymphocyte antigen 4 (CTLA-4, CD152), an immune modulatory molecule which is expressed on a subset of activated T-cells. The proposed mechanism of action for ipilimumab is the disruption of the interaction of CTLA-4 with B7 co-stimulatory molecules (CD80 or CD86) expressed on antigen presenting cells, which results in inhibition of the down-modulatory function of CTLA-4.

The cancer vaccine comprising SEQ ID NOS: 1, 2 and 3 is an injectable therapeutic cancer vaccine currently in development for treatment of several cancer types. It consists of a mixture of three synthetic peptides, 15 and 30 amino acids long, which represent fragments of the naturally occurring protein, human telomerase reverse transcriptase subunit (hTERT), and which are capable of inducing a cancer specific T helper cell response.

Clinical Trial
Design

This was a phase I/IIa, open label, single arm, interventional trial examining safety and tolerability for the ipilimumab/cancer vaccine combination in patients with unresectable or metastatic malignant melanoma.

Treatment Regime

Patients received ipilimumab and the cancer vaccine comprising SEQ ID NOS. 1, 2 and 3 together with Granulocyte Macrophage-Colony Stimulating Factor (GM-CSF). Ipilimumab was given every 3rd week for a total of 4 doses. GM-CSF and the cancer vaccine were given 7, 5 and 3 days before first dose of ipilimumab. The fourth dose of GM-CSF and the cancer vaccine was given 11 days after first dose of ipilimumab and then 3 days before each dose of ipilimumab and thereafter every 4th week for a total of up to 9 doses of vaccine.

Results

Of the 14 first patients enrolled in this study, 12 were eligible and treated. The patients had a mean age of 58.7 years (range 48-74). There were five women and seven men. Clinical response data with a follow up time of 5 to 14 months from start of treatment was collected and is shown in Table 8. Referring to Table 8, six of the twelve patients had a clinical response, three of these had a partial response and three had stable disease.

TABLE 8

Clinical response data
Best tumour response *

| N = 12 | CR | PR | SD | PD | Dead |
|---|---|---|---|---|---|
| Number of patients (%) | 0 | 3 (25) | 3 (25) | 4 (33) | 2 (17) |

* Based on clinical evaluation
CR: complete response; PR: partial response; SD: stable disease; PD: progressive disease.
Best tumour response is the best response recorded during the observation time.

Discussion

The results described above give a disease control rate (the proportion of patients with partial or complete response or stable disease) of 50%. Hodi et al. 2010 have reported results from a phase 3 study in a similar patient population where the disease control rate (best overall response) in the patient group receiving ipilimumab alone was 28.5% (median follow-up time was 27.8 months) and the disease control rate in the patient group receiving ipilimumab and the cancer vaccine gp100 was 20.1% (median follow-up time was 21 months) (Hodi et al. N Engl J Med. 2010 363(8):711-23). Importantly, the partial response rate in the current study was 25%. Hodi et al. 2010 reported partial response rates of 5.5% and 9.5% for the ipilimumab plus Gp100 group and the ipilimumab alone group respectively. Gp100 is a cancer vaccine comprising HLA-A*0201-restricted 9-mer peptides derived from the melanosomal protein, glycoprotein 100 (Gp100).

Therefore, the disease control rate observed in the clinical trial above, where patients with unresectable or metastatic malignant melanoma received a cancer vaccine comprising three long peptides from hTERT in combination with ipilimumab was clearly higher than that observed in a similar patient population when ipilimumab was administered alone or in combination with a cancer vaccine comprising a short (9-mer) peptide derived from gp100. In particular, the partial response rate of the clinical trial above was substantially higher than that reported by Hodi et al. 2010.

Example 8: Overall Survival Data from Patients with Unresectable or Metastatic Malignant Melanoma Who Received a Cancer Vaccine in Combination with Ipilimumab Introduction This Example provides further data from the clinical trial as set under Example 7.

Results

Of the 14 first patients enrolled in this study, 12 were eligible and treated. The patients had a mean age of 58.7 years (range 48-74). There were five women and seven men. The overall survival (OS) rate at 18 months and 12 months from randomization was 75% (9/12), Median overall survival had not yet been reached. However, with available follow-up data for survival ranging from 18 to 28 months, median overall survival was at least 18 months. In general, overall survival is defined as the length of time from randomization in the clinical study until death from any cause.

Discussion

Hodi et al. 2010 have reported results from a phase 3 study in a similar patient population where 1 year OS rate was 46% in the patient group receiving ipilimumab alone and 44% in the patient group receiving ipilimumab and the cancer vaccine gp100 (Hodi et al. N Engl J Med. 2010 363(8):711-23). Gp100 is a cancer vaccine comprising HLA-A*0201-restricted 9-mer peptides derived from the melanosomal protein, glycoprotein 100 (Gp100). Hadi reported median overall survival of 10.1 months in the ipilimumab alone group and 10.0 months in the ipilimumab plus gp100 group. The median follow-up time for survival was 27.8 months and 21 months in the patient groups receiving ipilimumab alone and ipilimumab plus gp100 respectively.

Therefore, the 1 year overall survival and median overall survival in the clinical trial above, where patients with unresectable or metastatic malignant melanoma received a cancer vaccine comprising three long peptides from hTERT in combination with ipilimumab were clearly higher than those observed in a similar patient population when ipilimumab was administered alone or in combination with a cancer vaccine comprising a short (9-mer) peptide derived from gp100.

Example 9: Induction of Immune Responses in Samples from Lung and Prostate Cancer Patients Who Received a Cancer Vaccine Alone Compared with Melanoma Patients Who Received a Cancer Vaccine in Combination with Ipilimumab The therapeutic cancer vaccine comprising SEQ. ID NOS. 1, 2 and 3 has been investigated in two phase 1/2A clinical trials in patients with lung cancer (EudraCT number: 2012-001852-20) and prostate cancer (EudraCT number: 2012-002411-26) respectively.

Combination treatment with the anti-CTLA-4 antibody ipilimumab and the cancer vaccine comprising SEQ. ID NOS. 1, 2 and 3 has been investigated in a clinical trial in melanoma (EudraCT number: 2013-005582-39).

Treatment Regime
Lung and Prostate Cancer Trials:

The studies were open labeled dose-escalating phase I/IIa studies of the cancer vaccine comprising SEQ. ID NOS. 1, 2 and 3 in patients with androgen-sensitive metastatic prostate cancer and non-small cell lung cancer (NSCLC) after completion of radiation therapy and/or chemotherapy respectively. The cancer vaccine comprising SEQ. ID NOS. 1, 2 and 3 and GM-CSF was given at days 1, 3 and 5, then at week 2, 3, 4, 6 and 8 followed by monthly vaccinations up to 6 months.

Melanoma Trial:

Patients with unresectable or metastatic malignant melanoma received ipilimumab and the cancer vaccine comprising SEQ. ID NOS. 1, 2 and 3 together with GM-CSF. Ipilimumab was given every 3rd week for a total of 4 doses according to standard procedure. The cancer vaccine comprising SEQ. ID NOS. 1, 2 and 3 and GM-CSF was given before and between treatments of ipilimumab and thereafter every 4th week for a total of up to 9 doses of vaccine. More specifically, the cancer vaccine comprising SEQ. ID NOS. 1, 2 and 3 and GM-CSF were given 7, 5 and 3 days before first dose of ipilimumab. The fourth dose of GM-CSF and the cancer vaccine was given 11 days after first dose of ipilimumab and then 3 days before each dose of ipilimumab and thereafter every 4th week for a total of up to 9 doses of vaccine.

Immune Response Analysis

Immune responses were measured by a T cell response assay (proliferation by 3H-thymidine incorporation) using patient blood samples harvested before, during and after treatment as per the Materials and Methods. The specific T-cell response was considered positive if the peptide response was at least 3 times the background (Stimulation Index, SI≥3) for at least one of the vaccine peptides or the combination of the peptides. Any patient who developed a positive specific T-cell response against any of the peptides of SEQ. ID NOS. 1, 2 or 3 during the study was defined as an immune responder.

Results

Immune response data following vaccination with 300 microgram of the cancer vaccine comprising SEQ. ID NOS. 1, 2 and 3 were available from 7 patients in the prostate cancer study and 6 patients from the lung cancer study. Blood samples from 11 patients in the melanoma study (i.e. 300 microgram of the cancer vaccine in combination with ipilimumab) were also available for immune response analysis. The data are summarised in FIG. 7.

Figure 7:
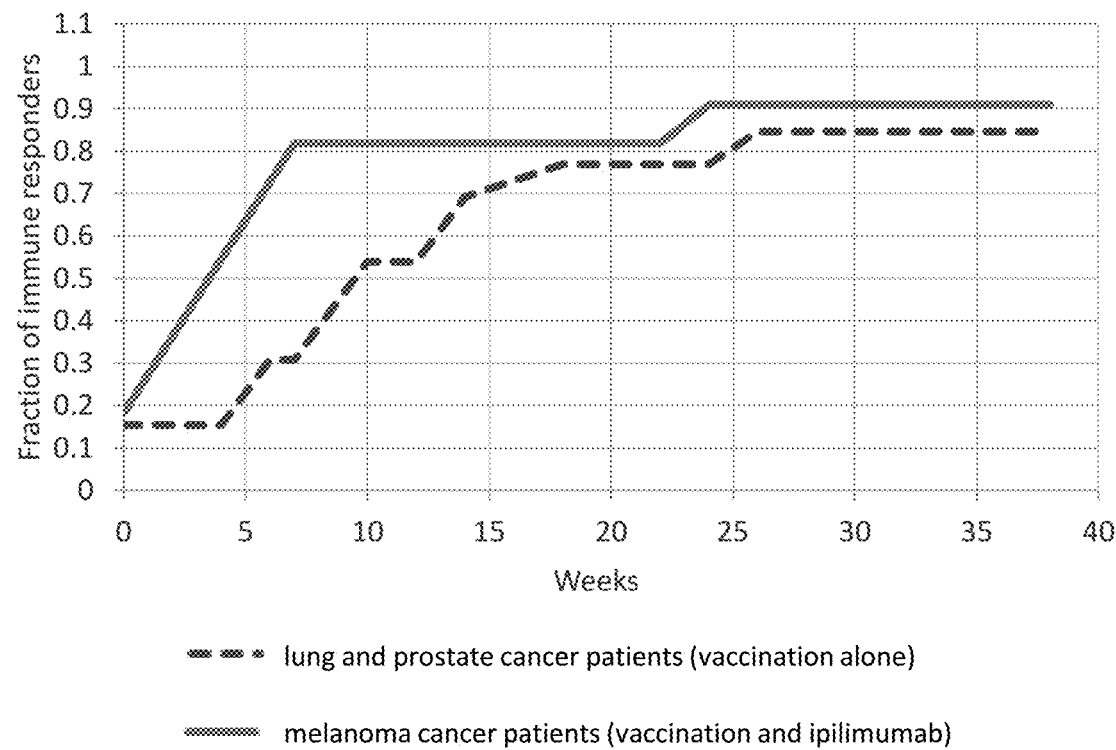
FIG. 7 is a graph summarising positive immune responses detected in samples from lung and prostate cancer patients vaccinated with SEQ ID NOS: 1, 2 and 3 and GM-CSF and in samples from melanoma patients receiving ipilimumab treatment in combination with vaccination with SEQ ID NOS: 1, 2 and 3 and GM-CSF. T cell proliferation was measured by 3H-thymidine incorporation. A stimulation index of was considered a positive immune response.

Referring to FIG. 7, the percentage of patients that developed a positive immune response against the vaccine at different time points following vaccination is shown. Overall, 10/11 (91%) patients in the melanoma trial had a positive immune response. For the one patient that did not have a positive response, only one post vaccination blood sample at 4 weeks was available. Overall, 86% of patients in the combined prostate and lung cancer groups had a positive immune response. The patients that received the combined treatment of the cancer vaccine and ipilimumab developed an immune response faster than the patients who received the cancer vaccine alone. At four weeks, 55% of the patients who received the combination of the cancer vaccine and ipilimumab had an immune response while it took 10 weeks before more than half (54%) of the patients who received the cancer vaccine alone developed an immune response. Two patients in the melanoma study, two patients in the prostate cancer study and one patient in the lung cancer study had a spontaneous immune response to one of the vaccine peptides, which were all strengthened by vaccination.

Therefore, the results of FIG. 7 demonstrate that patients who received the combined treatment of the cancer vaccine and ipilimumab mounted immune responses to the polypeptides of the vaccine faster than those patients who received the cancer vaccine alone. Overall, a higher proportion of the patients who received the combined treatment of the cancer vaccine and ipilimumab developed an immune response against one of the polypeptides of the vaccine over the course of the study, compared with those patients who received the cancer vaccine alone.

Example 10: Combining a Cancer Vaccine and Ipilimumab Produces a Synergistic Effect in the Treatment of Cancer The therapeutic cancer vaccine comprising SEQ. ID NOS. 1, 2 and 3 has been investigated in two phase 1/2A clinical trials in patients with lung cancer (EudraCT number: 2012-001852-20) and prostate cancer (EudraCT number: 2012-002411-26) respectively.

Combination treatment with the anti-CTLA-4 antibody ipilimumab and the cancer vaccine comprising SEQ. ID. NOS. 1, 2 and 3 has been investigated in a clinical trial in melanoma (EudraCT number: 2013-005582-39).

Treatment Regime

Lung and Prostate Cancer Trials:

The studies were open labeled dose-escalating phase I/IIa studies of the cancer vaccine comprising SEQ. ID NOS. 1, 2 and 3 in patients with androgen-sensitive metastatic prostate cancer and NSCLC after completion of radiation therapy and/or chemotherapy respectively. The cancer vaccine comprising SEQ. ID NOS. 1, 2 and 3 and GM-CSF was given at days 1, 3 and 5, then weeks 2, 3, 4, 6, 8 and 10 followed by monthly injections up to 6 months.

Melanoma Trial:

Patients with unresectable or metastatic malignant melanoma received ipilimumab and the cancer vaccine comprising SEC), ID NOS. 1, 2 and 3 together with GM-CSF. Ipilimumab was given every 3rd week for a total of 4 doses according to standard procedure. The cancer vaccine comprising SEQ. ID NOS. 1, 2 and 3 and GM-CSF was given before and between treatments of ipilimumab and thereafter every 4th week for a total of up to 9 doses of vaccine. More specifically, the cancer vaccine comprising SEQ. ID NOS. 1, 2 and 3 and GM-CSF were given 7, 5 and 3 days before first dose of ipilimumab. The fourth dose of GM-CSF and the cancer vaccine was given 11 days after first dose of ipilimumab and then 3 days before each dose of ipilimumab and thereafter every 4th week for a total of up to 9 doses of vaccine.

Immune Response Analysis

Immune responses were measured by a T cell response assay (proliferation by 3H-thymidine incorporation) using patient blood samples harvested before, during and after treatment as set out in the Materials and Methods. The specific T-cell response was considered positive if the peptide response was at least 3 times the background (Stimulation Index, SI 3) for at least one of the vaccine peptides or the combination of the peptides. Any patient who developed a positive specific T-cell response against any of the peptides of SEQ. ID NOS. 1, 2 or 3 during the study was defined as an immune responder.

Results

Lung and Prostate Cancer Trials:

Combined data for the 300 microgram dose cohort from the lung and prostate cancer trials are shown in Table 9A. Only data for responding patients are included. For the 11 responding patients out of the 13 vaccinated patients, an average of 7.6 cancer vaccine injections (range 6 to 11) per patient were required to obtain a positive immune response against at least one of the peptides of SEQ ID NOS. 1, 2 or 3 in the cancer vaccine. This corresponds to an average dose of 2.3 mg of the cancer vaccine (range 1.8 to 3.3 mg) per patient. The average strength (SI) of the peak immune response in this group of patients was 15.5 (range 3.7-34.5).

TABLE 9A

Data from patients in the lung and prostate clinical trials
Prostate and lung cancer

| Patient No. | No. of Injections | Amount Peptide (mg) | Peak IR |
|---|---|---|---|
| L1 | 11 | 3.3 | 3.7 |
| L2 | 7 | 2.1 | 15.5 |
| L3 | 7 | 2.1 | 3.8 |
| L4 | 9 | 2.7 | 19.4 |
| L5 | 7 | 2.1 | 6.4 |
| L6 | 8 | 2.4 | 5.8 |
| L7 | 6 | 1.8 | 34.5 |
| P1 | 6 | 1.8 | 39 |
| P2 | 8 | 2.4 | 4.7 |
| P3 | 8 | 2.4 | 31.6 |
| P4 | 7 | 2.1 | 6.2 |
| Avg | 7.6 | 2.3 | 15.5 |

IR: immune response;
L1-7: lung cancer patients;
P1-4: prostate cancer patients

Melanoma Trial:

In this study the same cancer vaccine dose (300 microgram per injection) was used. The data are shown in Table 9B. Ten of the eleven patients in this group mounted a positive immune response to the cancer vaccine following vaccination. The average number of cancer vaccine injections required to obtain a positive immune response in the 10 patients was 5 (range 3 to 7). This corresponds to an average dose of 1.5 mg of the cancer vaccine (range 0.9 to 2.1 mg) per patient. The average strength (SI) of the peak immune response in this group of patients was 20.2 (range 3.9 to 56.3).

TABLE 9B

Data from patients in the melanoma clinical trial
Melanoma & IPI

| Patient No. | No. of Injections | Amount Peptide (mg) | Peak IR |
|---|---|---|---|
| 1 | 7 | 2.1 | 3.9 |
| 2 | 5 | 1.5 | 56.3 |
| 3 | 7 | 2.1 | 5.5 |
| 4 | 7 | 2.1 | 15.2 |
| 5 | 5 | 1.5 | 10.9 |
| 6 | 5 | 1.5 | 7.8 |
| 7 | 5 | 1.5 | 25.9 |
| 8 | 3 | 0.9 | 41.3 |
| 9 | 3 | 0.9 | 7.8 |
| 11 | 3 | 0.9 | 27.2 |
| Avg | 5.0 | 1.5 | 20.2 |

IR: immune response

Discussion

The data presented in Tables 9A and 9B clearly demonstrate a synergistic effect when the cancer vaccine comprising SEQ. ID NOS. 1, 2 and 3 is combined with the CTLA-4 blocking agent ipilimumab in the treatment of cancer. This is both manifested by a significant reduction of the time required by the immune system of the patient to mount a measurable immune response to the vaccine (summarised in Table 9C) and by the subsequent strength of the immune response. In patients with a growing tumour mass, time is critical and an early immune response will be essential in getting control of the tumour. The time difference between 5 injections (15 days) and 7.6 (8) injections (36 days) is therefore highly relevant. Another important success parameter is the strength of the immune response. A strong immune response is more likely to have a clinical impact than a weak response, therefore the mean peak SI of 20.2 seen in the combination trial compares favourably to the mean peak SI of 15.5 observed when cancer vaccine was given alone.

TABLE 9C

Summary of data from patient in the lung, prostate and melanoma clinical trials

| Treatment | Indication | Number of injections to 1st positive immune response (SI ≥ 3) | Amount of cancer vaccine (mg) injected to 1st positive immune response | Peak Immune response (SI) |
|---|---|---|---|---|
| Cancer vaccine | prostate + lung | 7.6 | 2.3 | 15.5 |
| Cancer vaccine + ipi | melanoma | 5 | 1.5 | 20.2 |

In conclusion, the data from the analysis of the role of CTLA-4 blockade in combination with a long peptide-based vaccine (i.e. comprising polypeptides having the sequence of SEQ. ID NOS. 1, 2 and 3) provides for the first time an example of a synergistic effect when CTLA-4 blockade is combined with a peptide vaccine-induced T cell response in cancer patients. This synergistic effect comprised a reduction in the time taken for the patients to mount a positive immune response to a peptide of the vaccine; a stronger immune response; and an improved clinical response (i.e. as demonstrated by Example 7). Overall, these data provide a strong rationale for a new type of cancer vaccine-checkpoint inhibitor treatment that is expected to change further the clinical picture in cancer treatment.

Example 11: Induction of a Broad Immune Response in Samples from Melanoma Patients Who Received a Cancer Vaccine in Combination with Ipilimumab The therapeutic cancer vaccine comprising SEQ. ID NOS. 1, 2 and 3 has been investigated in two phase 1/2A clinical trials in patients with lung cancer (EudraCT number: 2012-001852-20) and prostate cancer (EudraCT number: 2012-002411-26) respectively.

Combination treatment with the anti-CTLA4 antibody ipilimumab and the cancer vaccine comprising SEQ. ID. NOS. 1, 2 and 3 has been investigated in a clinical trial in melanoma (EudraCT number: 2013-005582-39).

Treatment Regime
Lung and Prostate Cancer Trials:

The studies were open labeled dose-escalating phase I/IIa studies of the cancer vaccine comprising SEQ. ID NOS. 1, 2 and 3 in patients with androgen-sensitive metastatic prostate cancer and NSCLC after completion of radiation therapy and/or chemotherapy respectively. The cancer vaccine comprising SEQ. ID NOS. 1, 2 and 3 and GM-CSF was given at days 1, 3 and 5, then weeks 2, 3, 4, 6, 8 and 10 followed by monthly injections up to 6 months. There were three different dose groups with 100, 300 and 700 microgram vaccine while the adjuvant dose was 75 microgram GM-CSF.

Melanoma Trial:

Patients with unresectable or metastatic malignant melanoma received ipilimumab and the cancer vaccine comprising SEQ. ID NOS. 1, 2 and 3 together with GM-CSF. Ipilimumab was given every 3rd week for a total of 4 doses according to standard procedure. The cancer vaccine comprising SEQ. ID NOS. 1, 2 and 3 and GM-CSF was given before and between treatments of ipilimumab and thereafter every 4th week for a total of up to 9 doses of vaccine. The vaccine dose was 300 microgram while the adjuvant dose was 75 microgram GM-CSF.

Immune Response Analysis

Immune responses were measured by a T cell response assay (proliferation by 3H-thymidine incorporation) using patient blood samples harvested before, during and after treatment as set out in the Materials and Methods. The specific T-cell response was considered positive if the peptide response was at least 3 times the background (Stimulation Index, SI≥3). Immune responses were measured for each individual peptide of SEQ. ID NOS. 1, 2 or 3.

Results

The fraction of patients with a positive immune response for all of the individual peptides of SEQ. ID NOS. 1, 2 or 3 after vaccination is presented in Table 10 below.

TABLE 10

| Clinical study | Fraction of patients responding to all three vaccine peptides |
|---|---|
| Lung cancer | 4/18 (22%) |
| Prostate cancer | 3/21 (14%) |
| Malignant melanoma | 3/11 (27%) |

Discussion

As discussed in Example 9, 91% of melanoma patients who received the combined treatment of the cancer vaccine and ipilimumab developed an immune response against one of the polypeptides of the vaccine. The present Example further demonstrates that a broad immune response developed in melanoma patients who received the combined treatment of the cancer vaccine and ipilimumab. This is manifested by a larger fraction of patients developing an immune response against all three vaccination peptides of SEQ. ID NOS, 1, 2 and 3 when vaccination was combined with the CTLA4 blocking agent ipilimumab as compared to when vaccination was given alone (i.e. in the prostate and lung cancer patients). The data presented in Table 10 therefore further demonstrate a synergistic effect when the cancer vaccine comprising SEQ. ID NOS. 1, 2 and 3 is combined with the CTLA-4 blocking agent ipilimumab in the treatment of cancer. A broad immune response is known to be associated with favourable clinical outcome (Kenter et al. N Engl J Med. 2009 Nov. 5; 361(19):1838-47).

In conclusion, the data from Example 11 provide further evidence of a synergistic effect in the treatment of cancer, in the form of the induction of a broad immune response, when the cancer vaccine comprising SEQ. ID NOS. 1, 2 and 3 is combined with the CTLA-4 blocking agent ipilimumab.

Overall, the data in the aforementioned Examples demonstrate that combining a long peptide cancer vaccine against a self-antigen with an anti-CTLA-4 antibody results in the following advantages compared with administration of the vaccine alone: the number of patients responding to the vaccine is increased (91% of evaluable patients); the responses appear earlier and are stronger, requiring fewer vaccinations; and there is a higher proportion of patients able to mount an immune response against all 3 components of the vaccine (i.e. a broad immune response). This amplification of the vaccine response results in a higher clinical benefit when the combination is administered compared to when ipilimumab is administered alone.

| SEQ. ID NO. in Sequence Listing | Sequence | Notes |
|---|---|---|
| 1 | ALFSVLNYERARRPGLLGASVLGLDDIHRA | Corresponds to amino acid positions 660-689 in the hTERT protein |
| 2 | RTFVLRVRAQDPPPE | Corresponds to amino acid positions 691-705 in the hTERT protein |
| 3 | AERLTSRVKALFSVL | Corresponds to amino acid positions 651-665 in the hTERT protein |
| 4 | RLTSRVKALFSVLNY | Corresponds to amino acid positions 653-667 in the hTERT protein |
| 5 | EARPALLTSRLRFIPK | Corresponds to the GV1001 peptide |
| 6 | MPRAPRCRAVRSLLRSHYREVLPLATFVRRLGPQGWRLVQRGDPAAFRALVAQCLVC VPWDARPPPAAPSFRQVSCLKELVARVLQRLCERGAKNVLAFGFALLDGARGGPPEA FTTSVRSYLPNTVTDALRGSGAWGLLLRRVGDDVLVHLLARCALFVLVAPSCAYQVC GPPLYQLGAATQARPPPHASGPRRRLGCERAWNHSVREAGVPLGLPAPGARRRGGSA SRSLPLPKRPRRGAAPEPERTPVGQGSWAHPGRTRGPSDRGFCVVSPARPAEEATSL EGALSGTRHSHPSVGRQHHAGPPSTSRPPRPWDTPCPPVYAETKHFLYSSGDKEQLR PSFLLSSLRPSLTGARRLVETIFLGSRPWMPGTPRRLPRLPQRYWQMRPLFLELLGN HAQCPYGVLLKTHCPLRAAVTPAAGVCAREKPQGSVAAPEEEDTDPRRLVQLLRQHS SPWQVYGFVRACLRRLVPPGLWGSRHNERRFLRNTKKFISLGKHAKLSLQELTWKMS VRDCAWLRRSPGVGCVPAAEHRLREEILAKFLHWLMSVYVVELLRSFFYVTETTFQK NRLFFYRKSVWSKLQSIGIRQHLKRVQLRELSEAEVRQHREARPALLTSRLRFIPKP DGLRPIVNMDYVVGARTFRREKRAERLTSRVKALFSVLNYERARRPGLLGASVLGLD DIHRAWRTFVLRVRAQDPPPELYFVKVDVTGAYDTIPQDRLTEVIASIIKPQNTYCV RRYAVVQKAAHGHVRKAFKSHVSTLTDLQPYMRQFVAHLQETSPLRDAVVIEQSSSL NEASSGLFDVFLRFMCHHAVRIRGKSYVQCQGIPQGSILSTLLCSLCYGDMENKLFA GIRRDGLLLRLVDDFLLVTPHLTHAKTFLRTLVRGVPEYGCVVNLRKTVVNFPVEDE ALGGTAFVQMPAHGLFPWCGLLLDTRTLEVQSDYSSYARTSIRASLTFNRGFKAGRN MRRKLFGVLRLKCHSLFLDLQVNSLQTVCTNIYKILLLQAYRFHACVLQLPFHQQVW KNPTFFLRVISDTASLCYSILKAKNAGMSLGAKGAAGPLPSEAVQWLCHQAFLLKLT RHRVTYVPLLGSLRTAQTQLSRKLPGTTLTALEAAANPALPSDFKTILD | hTERT amino acid sequence |
| 7 | ALFSVLNYERARRP | Fragment of SEQ ID NO: 1- Corresponds to amino acid positions 660-673 in the hTERT protein |
| 8 | LFSVLNYERARRPG | Fragment of SEQ ID NO: 1- Corresponds to amino acid positions 661-674 in the hTERT protein |
| 9 | FSVLNYERARRPGL | Fragment of SEQ ID NO: 1- Corresponds to amino acid positions 662-675 in the hTERT protein |
| 10 | SVLNYERARRPGLL | Fragment of SEQ ID NO: 1- Corresponds to amino acid positions 663-676 in the hTERT protein |
| 11 | VLNYERARRPGLLG | Fragment of SEQ ID NO: 1- Corresponds to amino acid positions 664-677 in the hTERT protein |
| 12 | LNYERARRPGLLGA | Fragment of SEQ ID NO: 1- Corresponds to amino acid positions 665-678 in the hTERT protein |
| 13 | NYERARRPGLLGAS | Fragment of SEQ ID NO: 1- Corresponds to amino acid positions 666-679 in the hTERT protein |
| 14 | YERARRPGLLGASV | Fragment of SEQ ID NO: 1- Corresponds to amino acid positions 667-680 in the hTERT protein |
| 15 | ERARRPGLLGASVL | Fragment of SEQ ID NO: 1- Corresponds to amino acid positions 668-681 in the hTERT protein |
| 16 | RARRPGLLGASVLG | Fragment of SEQ ID NO: 1- Corresponds to amino acid positions 669-682 in the hTERT protein |

| SEQ. ID NO. in Sequence Listing | Sequence | Notes |
| --- | --- | --- |
| 17 | ARRPGLLGASVLGL | Fragment of SEQ ID NO: 1- Corresponds to amino acid positions 670-683 in the hTERT protein |
| 18 | RRPGLLGASVLGLD | Fragment of SEQ ID NO: 1- Corresponds to amino acid positions 671-684 in the hTERT protein |
| 19 | RPGLLGASVLGLDD | Fragment of SEQ ID NO: 1- Corresponds to amino acid positions 672-685 in the hTERT protein |
| 20 | PGLLGASVLGLDDI | Fragment of SEQ ID NO: 1- Corresponds to amino acid positions 673-686 in the hTERT protein |
| 21 | GLLGASVLGLDDIH | Fragment of SEQ ID NO: 1- Corresponds to amino acid positions 674-687 in the hTERT protein |
| 22 | LLGASVLGLDDIHR | Fragment of SEQ ID NO: 1- Corresponds to amino acid positions 675-688 in the hTERT protein |
| 23 | LGASVLGLDDIHRA | Fragment of SEQ ID NO: 1- Corresponds to amino acid positions 676-689 in the hTERT protein |
| 24 | SVLNYERARRPGLLG | Fragment of SEQ ID NO: 1- Corresponds to amino acid positions 663-677 in the hTERT protein |
| 25 | FSVLNYERARRPGLL | Fragment of SEQ ID NO: 1- Corresponds to amino acid positions 662-676 in the hTERT protein |
| 26 | ARRPGLLGASVLGLD | Fragment of SEQ ID NO: 1- Corresponds to amino acid positions 670-684 in the hTERT protein |
| 27 | RARRPGLLGASVLGL | Fragment of SEQ ID NO: 1- Corresponds to amino acid positions 669-683 in the hTERT protein |
| 28 | VLNYERARRPGLLGA | Fragment of SEQ ID NO: 1- Corresponds to amino acid positions 664-678 in the hTERT protein |
| 29 | RPGLLGASVLGLDDI | Fragment of SEQ ID NO: 1- Corresponds to amino acid positions 671-685 in the hTERT protein |
| 30 | VLNYERARRPGLLGA | Fragment of SEQ ID NO: 1- Corresponds to amino acid positions 664-678 in the hTERT protein |
| 31 | RTFVLRVRAQDP | Fragment of SEQ ID NO: 2- Corresponds to amino acid positions 691-702 in the hTERT protein |
| 32 | TFVLRVRAQDPP | Fragment of SEQ ID NO: 2- Corresponds to amino acid positions 692-703 in the hTERT protein |
| 33 | FVLRVRAQDPPP | Fragment of SEQ ID NO: 2- Corresponds to amino acid positions 693-704 in the hTERT protein |
| 34 | VLRVRAQDPPPE | Fragment of SEQ ID NO: 2- Corresponds to amino acid positions 694-705 in the hTERT protein |

| SEQ. ID NO. in Sequence Listing | Sequence | Notes |
|---|---|---|
| 35 | AERLTSRVKALF | Fragment of SEQ ID NO: 3- Corresponds to amino acid positions 651-662 in the hTERT protein |
| 36 | ERLTSRVKALFS | Fragment of SEQ ID NO: 3- Corresponds to amino acid positions 652-663 in the hTERT protein |
| 37 | RLTSRVKALFSV | Fragment of SEQ ID NO: 3- Corresponds to amino acid positions 653-664 in the hTERT protein |
| 38 | LTSRVKALFSVL | Fragment of SEQ ID NO: 3- Corresponds to amino acid positions 654-665 in the hTERT protein |

The invention claimed is:

1. A method of treatment of cancer in a patient, comprising the steps of:
   i) inhibiting an immune checkpoint by administering at least one immune checkpoint inhibitor, wherein the at least one immune checkpoint inhibitor is selected from the group consisting of an anti-CTLA-4 antibody or an antigen-binding fragment thereof, an anti-PD-1 antibody or an antigen-binding fragment thereof and an anti-PD-L1 antibody or an antigen-binding fragment thereof, and wherein the at least one immune checkpoint inhibitor down-regulates or blocks the immune checkpoint; and
   ii) simultaneously, separately or sequentially administering: a cocktail of polypeptides comprising:
   a) a polypeptide consisting of a sequence of SEQ ID NO. 1 or a fragment thereof comprising at least 12 amino acids;
   b) a polypeptide consisting of a sequence of SEQ ID NO. 2 or a fragment thereof comprising at least 12 amino acids; and
   c) a polypeptide consisting of a sequence of SEQ ID NO. 3 or a fragment thereof comprising at least 12 amino acids,
   wherein the method produces a synergistic effect in the treatment of cancer in the patient.

2. The method according to claim 1, wherein the synergistic effect comprises an improved clinical outcome in the patient.

3. The method according to claim 2, wherein the improved clinical outcome is one or more of an improved overall survival and/or an improved effect on tumour size or on the extent of tumour in the body as compared to that obtained with a method in which only an immune checkpoint is inhibited or only the cocktail of polypeptides is administered.

4. The method according to claim 1, wherein steps i) and ii) are performed within 4 months of each other.

5. The method according to claim 1, wherein the anti-CTLA-4 antibody is selected from the group consisting of ipilimumab and tremelimumab.

6. The method according to claim 1, wherein the anti-PD-1 antibody is selected from the group consisting of nivolumab and pembrolizumab.

7. The method according to claim 1, wherein the anti-PD-L1 antibody is selected from the group consisting of MPDL3280A, MEDI4736, and BMS-936559.

8. The method according to claim 1, wherein the fragment of SEQ ID NO. 1 comprises at least 14 amino acids or at least 20 amino acids, and/or the fragment of SEQ ID NO. 2 comprises at least 14 amino acids and/or the fragment of SEQ ID NO. 3 comprises at least 14 amino acids.

9. The method according to claim 1, wherein the cocktail of polypeptides comprises a polypeptide consisting of the sequence of SEQ ID NO. 1, a polypeptide consisting of the sequence of SEQ ID NO. 2 and a polypeptide consisting of the sequence of SEQ ID NO. 3.

10. The method according to claim 1, wherein step i) comprises the step of administering a first and a second immune checkpoint inhibitor.

11. The method according to claim 10, wherein the first immune checkpoint inhibitor is an anti-CTLA-4 antibody or an antigen-binding fragment thereof and wherein the second immune checkpoint inhibitor is an anti-PD-1 antibody or an antigen-binding fragment thereof.

12. The method according to claim 11, wherein the anti-CTLA-4 antibody is ipilimumab and the anti-PD-1 antibody is nivolumab.

13. The method according to claim 1, wherein step i) and/or ii) is performed simultaneously, separately or sequentially with the administration of a further therapeutic ingredient to the patient.

14. The method according to claim 1, wherein step ii) is performed simultaneously, separately or sequentially with the administration of an adjuvant and wherein the adjuvant is granulocyte-macrophage colony-stimulating factor (GM-CSF).

15. The method according to claim 1, wherein a polypeptide in the cocktail of polypeptides is linked to a further substance.

16. The method according to claim 1, wherein the cancer is one or more selected from the group consisting of melanoma, lung cancer, ovarian cancer, prostate cancer, pancreatic cancer, glioblastoma, colon cancer and head and neck cancer.

17. The method according to claim 16, wherein the melanoma is unresectable or metastatic melanoma, and/or wherein the lung cancer is non-small cell lung cancer, and/or wherein the prostate cancer is metastatic prostate cancer.

18. A method of vaccination for cancer in a patient, comprising the steps of:
  i) inhibiting an immune checkpoint by administering at least one immune checkpoint inhibitor, wherein the at least one immune checkpoint inhibitor is selected from the group consisting of an anti-CTLA-4 antibody or an antigen-binding fragment thereof, an anti-PD-1 antibody or an antigen-binding fragment thereof and an anti-PD-L1 antibody or an antigen-binding fragment thereof, and wherein the at least one immune checkpoint inhibitor down-regulates or blocks the immune checkpoint; and
  ii) simultaneously, separately or sequentially administering: a cocktail of polypeptides comprising:
  a) a polypeptide consisting of a sequence of SEQ ID NO. 1 or a fragment thereof comprising at least 12 amino acids;
  b) a polypeptide consisting of a sequence of SEQ ID NO. 2 or a fragment thereof comprising at least 12 amino acids; and
  c) a polypeptide consisting of a sequence of SEQ ID NO. 3 or a fragment thereof comprising at least 12 amino acids,
  wherein the method produces a synergistic effect in the vaccination for cancer in the patient.

19. The method according to claim 18, wherein steps i) and ii) are performed within 4 months of each other.

20. The method according to claim 18, wherein the anti-CTLA-4 antibody is selected from the group consisting of ipilimumab and tremelimumab.

21. The method according to claim 18, wherein the anti-PD-1 antibody is selected from the group consisting of nivolumab and pembrolizumab.

22. The method according to claim 18, wherein the anti-PD-L1 antibody is selected from the group consisting of MPDL3280A, MEDI4736, and BMS-936559.

23. The method according to claim 18, wherein the fragment of SEQ ID NO. 1 comprises at least 14 amino acids or at least 20 amino acids, and/or the fragment of SEQ ID NO. 2 comprises at least 14 amino acids and/or the fragment of SEQ ID NO. 3 comprises at least 14 amino acids.

24. The method according to claim 18, wherein the cocktail of polypeptides comprises a polypeptide consisting of the sequence of SEQ ID NO. 1, a polypeptide consisting of the sequence of SEQ ID NO. 2 and a polypeptide consisting of the sequence of SEQ ID NO. 3.

25. The method according to claim 18, wherein step i) comprises the step of administering a first and a second immune checkpoint inhibitor.

26. The method according to claim 25, wherein the first immune checkpoint inhibitor is an anti-CTLA-4 antibody or an antigen-binding fragment thereof and wherein the second immune checkpoint inhibitor is an anti-PD-1 antibody or an antigen-binding fragment thereof.

27. The method according to claim 26, wherein the anti-CTLA-4 antibody is ipilimumab and the anti-PD-1 antibody is nivolumab.

28. The method according to claim 18, wherein step i) and/or ii) is performed simultaneously, separately or sequentially with the administration of a further therapeutic ingredient to the patient.

29. The method according to claim 18, wherein step ii) is performed simultaneously, separately or sequentially with the administration of an adjuvant and wherein the adjuvant is granulocyte-macrophage colony-stimulating factor (GM-CSF).

30. The method according to claim 18, wherein a polypeptide in the cocktail of polypeptides is linked to a further substance.

31. The method according to claim 18, wherein the cancer is one or more selected from the group consisting of melanoma, lung cancer, ovarian cancer, prostate cancer, pancreatic cancer, glioblastoma, colon cancer and head and neck cancer.

32. The method according to claim 31, wherein the melanoma is unresectable or metastatic melanoma, and/or wherein the lung cancer is non-small cell lung cancer, and/or wherein the prostate cancer is metastatic prostate cancer.

* * * * *

SEQUENCE LISTING

```
Sequence total quantity: 38
SEQ ID NO: 1            moltype = AA   length = 30
FEATURE                 Location/Qualifiers
source                  1..30
                        mol_type = protein
                        organism = Homo sapiens
SEQUENCE: 1
ALFSVLNYER ARRPGLLGAS VLGLDDIHRA                                        30

SEQ ID NO: 2            moltype = AA   length = 15
FEATURE                 Location/Qualifiers
source                  1..15
                        mol_type = protein
                        organism = Homo sapiens
SEQUENCE: 2
RTFVLRVRAQ DPPPE                                                        15

SEQ ID NO: 3            moltype = AA   length = 15
FEATURE                 Location/Qualifiers
source                  1..15
                        mol_type = protein
                        organism = Homo sapiens
SEQUENCE: 3
AERLTSRVKA LFSVL                                                        15

SEQ ID NO: 4            moltype = AA   length = 15
FEATURE                 Location/Qualifiers
source                  1..15
                        mol_type = protein
                        organism = Homo sapiens
SEQUENCE: 4
RLTSRVKALF SVLNY                                                        15

SEQ ID NO: 5            moltype = AA   length = 16
FEATURE                 Location/Qualifiers
source                  1..16
                        mol_type = protein
                        organism = Homo sapiens
SEQUENCE: 5
EARPALLTSR LRFIPK                                                       16

SEQ ID NO: 6            moltype = AA   length = 1132
FEATURE                 Location/Qualifiers
source                  1..1132
                        mol_type = protein
                        organism = Homo sapiens
SEQUENCE: 6
MPRAPRCRAV RSLLRSHYRE VLPLATFVRR LGPQGWRLVQ RGDPAAFRAL VAQCLVCVPW    60
DARPPPAAPS FRQVSCLKEL VARVLQRLCE RGAKNVLAFG FALLDGARGG PPEAFTTSVR   120
SYLPNTVTDA LRGSGAWGLL LRRVGDDVLV HLLARCALFV LVAPSCAYQV CGPPLYQLGA   180
ATQARPPPHA SGPRRRLGCE RAWNHSVREA GVPLGLPAPG ARRRGGSASR SLPLPKRPRR   240
```

```
GAAPEPERTP VGQGSWAHPG RTRGPSDRGF CVVSPARPAE EATSLEGALS GTRHSHPSVG   300
RQHHAGPPST SRPPRPWDTP CPPVYAETKH FLYSSGDKEQ LRPSFLLSSL RPSLTGARRL   360
VETIFLGSRP WMPGTPRRLP RLPQRYWQMR PLFLELLGNH AQCPYGVLLK THCPLRAAVT   420
PAAGVCAREK PQGSVAAPEE EDTDPRRLVQ LLRQHSSPWQ VYGFVRACLR RLVPPGLWGS   480
RHNERRFLRN TKKFISLGKH AKLSLQELTW KMSVRDCAWL RRSPGVGCVP AAEHRLREEI   540
LAKFLHWLMS VYVVELLRSF FYVTETTFQK NRLFFYRKSV WSKLQSIGIR QHLKRVQLRE   600
LSEAEVRQHR EARPALLTSR LRFIPKPDGL RPIVNMDYVV GARTFRREKR AERLTSRVKA   660
LFSVLNYERA RRPGLLGASV LGLDDIHRAW RTFVLRVRAQ DPPPELYFVK VDVTGAYDTI   720
PQDRLTEVIA SIIKPQNTYC VRRYAVVQKA AHGHVRKAFK SHVSTLTDLQ PYMRQFVAHL   780
QETSPLRDAV VIEQSSSLNE ASSGLFDVFL RFMCHHAVRI RGKSYVQCQG IPQGSILSTL   840
LCSLCYGDME NKLFAGIRRD GLLLRLVDDF LLVTPHLTHA KTFLRTLVRG VPEYGCVVNL   900
RKTVVNFPVE DEALGGTAFV QMPAHGLFPW CGLLLDTRTL EVQSDYSSYA RTSIRASLTF   960
NRGFKAGRNM RRKLFGVLRL KCHSLFLDLQ VNSLQTVCTN IYKILLLQAY RFHACVLQLP  1020
FHQQVWKNPT FFLRVISDTA SLCYSILKAK NAGMSLGAKG AAGPLPSEAV QWLCHQAFLL  1080
KLTRHRVTYV PLLGSLRTAQ TQLSRKLPGT TLTALEAAAN PALPSDFKTI LD          1132

SEQ ID NO: 7             moltype = AA   length = 14
FEATURE                  Location/Qualifiers
source                   1..14
                         mol_type = protein
                         organism = Homo sapiens
SEQUENCE: 7
ALFSVLNYER ARRP                                                     14

SEQ ID NO: 8             moltype = AA   length = 14
FEATURE                  Location/Qualifiers
source                   1..14
                         mol_type = protein
                         organism = Homo sapiens
SEQUENCE: 8
LFSVLNYERA RRPG                                                     14

SEQ ID NO: 9             moltype = AA   length = 14
FEATURE                  Location/Qualifiers
source                   1..14
                         mol_type = protein
                         organism = Homo sapiens
SEQUENCE: 9
FSVLNYERAR RPGL                                                     14

SEQ ID NO: 10            moltype = AA   length = 14
FEATURE                  Location/Qualifiers
source                   1..14
                         mol_type = protein
                         organism = Homo sapiens
SEQUENCE: 10
SVLNYERARR PGLL                                                     14

SEQ ID NO: 11            moltype = AA   length = 14
FEATURE                  Location/Qualifiers
source                   1..14
                         mol_type = protein
                         organism = Homo sapiens
SEQUENCE: 11
VLNYERARRP GLLG                                                     14

SEQ ID NO: 12            moltype = AA   length = 14
FEATURE                  Location/Qualifiers
source                   1..14
                         mol_type = protein
                         organism = Homo sapiens
SEQUENCE: 12
LNYERARRPG LLGA                                                     14

SEQ ID NO: 13            moltype = AA   length = 14
FEATURE                  Location/Qualifiers
source                   1..14
                         mol_type = protein
                         organism = Homo sapiens
SEQUENCE: 13
NYERARRPGL LGAS                                                     14

SEQ ID NO: 14            moltype = AA   length = 14
FEATURE                  Location/Qualifiers
source                   1..14
                         mol_type = protein
                         organism = Homo sapiens
SEQUENCE: 14
YERARRPGLL GASV                                                     14
```

```
SEQ ID NO: 15           moltype = AA  length = 14
FEATURE                 Location/Qualifiers
source                  1..14
                        mol_type = protein
                        organism = Homo sapiens
SEQUENCE: 15
ERARRPGLLG ASVL                                                         14

SEQ ID NO: 16           moltype = AA  length = 14
FEATURE                 Location/Qualifiers
source                  1..14
                        mol_type = protein
                        organism = Homo sapiens
SEQUENCE: 16
RARRPGLLGA SVLG                                                         14

SEQ ID NO: 17           moltype = AA  length = 14
FEATURE                 Location/Qualifiers
source                  1..14
                        mol_type = protein
                        organism = Homo sapiens
SEQUENCE: 17
ARRPGLLGAS VLGL                                                         14

SEQ ID NO: 18           moltype = AA  length = 14
FEATURE                 Location/Qualifiers
source                  1..14
                        mol_type = protein
                        organism = Homo sapiens
SEQUENCE: 18
RRPGLLGASV LGLD                                                         14

SEQ ID NO: 19           moltype = AA  length = 14
FEATURE                 Location/Qualifiers
source                  1..14
                        mol_type = protein
                        organism = Homo sapiens
SEQUENCE: 19
RPGLLGASVL GLDD                                                         14

SEQ ID NO: 20           moltype = AA  length = 14
FEATURE                 Location/Qualifiers
source                  1..14
                        mol_type = protein
                        organism = Homo sapiens
SEQUENCE: 20
PGLLGASVLG LDDI                                                         14

SEQ ID NO: 21           moltype = AA  length = 14
FEATURE                 Location/Qualifiers
source                  1..14
                        mol_type = protein
                        organism = Homo sapiens
SEQUENCE: 21
GLLGASVLGL DDIH                                                         14

SEQ ID NO: 22           moltype = AA  length = 14
FEATURE                 Location/Qualifiers
source                  1..14
                        mol_type = protein
                        organism = Homo sapiens
SEQUENCE: 22
LLGASVLGLD DIHR                                                         14

SEQ ID NO: 23           moltype = AA  length = 14
FEATURE                 Location/Qualifiers
source                  1..14
                        mol_type = protein
                        organism = Homo sapiens
SEQUENCE: 23
LGASVLGLDD IHRA                                                         14

SEQ ID NO: 24           moltype = AA  length = 15
FEATURE                 Location/Qualifiers
source                  1..15
                        mol_type = protein
                        organism = Homo sapiens
SEQUENCE: 24
```

SVLNYERARR PGLLG                                                             15

SEQ ID NO: 25           moltype = AA   length = 15
FEATURE                 Location/Qualifiers
source                  1..15
                        mol_type = protein
                        organism = Homo sapiens SEQUENCE: 25
FSVLNYERAR RPGLL                                                             15

SEQ ID NO: 26           moltype = AA   length = 15
FEATURE                 Location/Qualifiers
source                  1..15
                        mol_type = protein
                        organism = Homo sapiens SEQUENCE: 26
ARRPGLLGAS VLGLD                                                             15

SEQ ID NO: 27           moltype = AA   length = 15
FEATURE                 Location/Qualifiers
source                  1..15
                        mol_type = protein
                        organism = Homo sapiens SEQUENCE: 27
RARRPGLLGA SVLGL                                                             15

SEQ ID NO: 28           moltype = AA   length = 15
FEATURE                 Location/Qualifiers
source                  1..15
                        mol_type = protein
                        organism = Homo sapiens SEQUENCE: 28
VLNYERARRP GLLGA                                                             15

SEQ ID NO: 29           moltype = AA   length = 15
FEATURE                 Location/Qualifiers
source                  1..15
                        mol_type = protein
                        organism = Homo sapiens SEQUENCE: 29
RPGLLGASVL GLDDI                                                             15

SEQ ID NO: 30           moltype = AA   length = 15
FEATURE                 Location/Qualifiers
source                  1..15
                        mol_type = protein
                        organism = Homo sapiens SEQUENCE: 30
VLNYERARRP GLLGA                                                             15

SEQ ID NO: 31           moltype = AA   length = 12
FEATURE                 Location/Qualifiers
source                  1..12
                        mol_type = protein
                        organism = Homo sapiens SEQUENCE: 31
RTFVLRVRAQ DP                                                                12

SEQ ID NO: 32           moltype = AA   length = 12
FEATURE                 Location/Qualifiers
source                  1..12
                        mol_type = protein
                        organism = Homo sapiens SEQUENCE: 32
TFVLRVRAQD PP                                                                12

SEQ ID NO: 33           moltype = AA   length = 12
FEATURE                 Location/Qualifiers
source                  1..12
                        mol_type = protein
                        organism = Homo sapiens SEQUENCE: 33
FVLRVRAQDP PP                                                                12

SEQ ID NO: 34           moltype = AA   length = 12
FEATURE                 Location/Qualifiers
source                  1..12
                        mol_type = protein
                        organism = Homo sapiens

```
SEQUENCE: 34
VLRVRAQDPP PE                                                                       12

SEQ ID NO: 35          moltype = AA  length = 12
FEATURE                Location/Qualifiers
source                 1..12
                       mol_type = protein
                       organism = Homo sapiens
SEQUENCE: 35
AERLTSRVKA LF                                                                       12

SEQ ID NO: 36          moltype = AA  length = 12
FEATURE                Location/Qualifiers
source                 1..12
                       mol_type = protein
                       organism = Homo sapiens
SEQUENCE: 36
ERLTSRVKAL FS                                                                       12

SEQ ID NO: 37          moltype = AA  length = 12
FEATURE                Location/Qualifiers
source                 1..12
                       mol_type = protein
                       organism = Homo sapiens
SEQUENCE: 37
RLTSRVKALF SV                                                                       12

SEQ ID NO: 38          moltype = AA  length = 12
FEATURE                Location/Qualifiers
source                 1..12
                       mol_type = protein
                       organism = Homo sapiens
SEQUENCE: 38
LTSRVKALFS VL                                                                       12
```